US012033731B2

(12) United States Patent
Meltabarger et al.

(10) Patent No.: US 12,033,731 B2
(45) Date of Patent: Jul. 9, 2024

(54) MEDICAL PROCESSING SYSTEMS AND METHODS

(71) Applicant: Express Scripts Strategic Development, Inc., St. Louis, MO (US)

(72) Inventors: Logan R. Meltabarger, St. Charles, MO (US); Pritesh J. Shah, Paramus, NJ (US); Amit K. Bothra, St. Louis, MO (US); David A. Tomala, Seattle, WA (US); Christopher R. Markson, Hawthorne, NJ (US); Bose S. Daggubati, St. Peters, MO (US); Christopher G. Lehmuth, St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 751 days.

(21) Appl. No.: 17/168,745

(22) Filed: Feb. 5, 2021

(65) Prior Publication Data
US 2021/0158919 A1 May 27, 2021

Related U.S. Application Data

(63) Continuation of application No. 15/498,048, filed on Apr. 26, 2017, now abandoned.
(Continued)

(51) Int. Cl.
*G06F 40/00* (2020.01)
*G16H 10/60* (2018.01)

(52) U.S. Cl.
CPC ................. *G16H 10/60* (2018.01)

(58) Field of Classification Search
CPC ...... G06F 40/00; G06F 40/103; G06F 40/117; G06F 40/126; G06F 40/16; G06F 40/174;
(Continued)

(56) References Cited

U.S. PATENT DOCUMENTS 5,664,109 A 9/1997 Johnson
5,801,697 A 9/1998 Parikh
(Continued)

OTHER PUBLICATIONS

Broß, Jürgen. Aspect-oriented sentiment analysis of customer reviews using distant supervision techniques. Diss. 2013.
(Continued)

*Primary Examiner* — Qi Han
(74) *Attorney, Agent, or Firm* — Miller Johnson

(57) ABSTRACT

A content analysis system includes a processor executing instructions from memory. The instructions include, in response to receiving a request signal from a user device, obtaining feedback items, each having a source indicator; identifying unique source indicators; and, for each source indicator, aggregating corresponding ones of the feedback items. A set of filtered feedback items is generated according to either first or second access levels associated with a user of the user device. A subset of filtered feedback items is selected according to a date range specified by the request signal, a set of automated rules is applied, and natural language processing is performed based on frequency of presence of salient terms to identify themes. A control signal is transmitted to a user interface of the user device instructing display of a representation that indicates a change in the frequency of the identified themes over the specified date range.

16 Claims, 13 Drawing Sheets

Related U.S. Application Data

(60) Provisional application No. 62/327,994, filed on Apr. 26, 2016.

(58) Field of Classification Search
CPC ........ G06F 40/177; G06F 40/18; G06F 40/20; G06F 40/205; G06F 40/211; G06F 40/216; G06F 40/247; G06F 40/253; G06F 40/30; G06F 40/56
USPC .................................. 704/1, 2, 4, 9, 10, 257
See application file for complete search history.

(56) References Cited

U.S. PATENT DOCUMENTS

| | | | |
|---|---|---|---|
| 6,112,986 | A | 9/2000 | Berger |
| 7,617,203 | B2 | 11/2009 | Awadallah |
| 7,756,726 | B2 | 7/2010 | Thuerk |
| 7,761,480 | B2 | 7/2010 | Toledano |
| 8,275,850 | B2 | 9/2012 | Kohan |
| 8,666,926 | B1 | 3/2014 | Nease |
| 8,818,788 | B1 | 8/2014 | Mihalik |
| 9,268,906 | B2 | 2/2016 | Curran |
| 9,319,449 | B2 | 4/2016 | Harpster |
| 9,426,051 | B2 | 8/2016 | Chakrabarti |
| 10,198,431 | B2 | 2/2019 | Somasundaran |
| 2004/0122656 | A1 | 6/2004 | Abir |
| 2007/0203996 | A1 | 8/2007 | Davitz |
| 2007/0223699 | A1 | 9/2007 | Jones |
| 2008/0046292 | A1 | 2/2008 | Myers |
| 2009/0119275 | A1 | 5/2009 | Chen |
| 2010/0010968 | A1 | 1/2010 | Redlich |
| 2010/0161652 | A1 | 6/2010 | Bellare |
| 2012/0179752 | A1 | 7/2012 | Mosley |
| 2012/0330995 | A1* | 12/2012 | Muenkel ................. G06F 40/18 715/219 |
| 2013/0187926 | A1 | 7/2013 | Silverstein |
| 2013/0232263 | A1 | 9/2013 | Kelly |
| 2014/0013451 | A1* | 1/2014 | Kulka ..................... G06F 21/14 726/29 |
| 2014/0304582 | A1* | 10/2014 | Bills ..................... H04W 4/029 715/224 |
| 2015/0189086 | A1 | 7/2015 | Romano |
| 2016/0259844 | A1 | 9/2016 | Trapeznikov |
| 2016/0316367 | A1* | 10/2016 | Rose .................... H04B 5/0056 |
| 2016/0335345 | A1 | 11/2016 | Wang |
| 2017/0250959 | A1 | 8/2017 | Gordon |
| 2017/0323065 | A1 | 11/2017 | Proctor Beauchamp |
| 2018/0253650 | A9 | 9/2018 | Liang |
| 2019/0179903 | A1 | 6/2019 | Terry |
| 2019/0180195 | A1 | 6/2019 | Terry |
| 2019/0180196 | A1 | 6/2019 | Terry |
| 2022/0188700 | A1 | 6/2022 | Khavronin |

OTHER PUBLICATIONS

Thornton, Chris, et al. "Auto-WEKA: Combined selection and hyperparameter optimization of classification algorithms." Proceedings of the 19th ACM SIGKDD international conference on Knowledge discovery and data mining. 2013.

Chen, et al. Proposal of LOA-based Sentiment Visualization of Hotel Reviews (Year: 2015).

Pedregosa, Fabian. "Hyperparameter optimization with approximate gradient." International conference on machine earning. PMLR, 2016.

Wei, Xing, and W. Bruce Croft. "LDA-based document models for ad-hoc retrieval." Proceedings of the 29th annual international ACM SIGIR conference on Research and development in information retrieval. 2006.

Wallach, Structured Topic Models for Language; Thesis, Newnham College, University of Cambridge (Year: 2008).

Wang; Structured Topic Models for Language: Jointly Modeling Words and Their Accompanying Modalities; (Year: 2009) A Dissertation submitted to Graduate School of the University of Massachusetts Amherst.

* cited by examiner

MEDICAL PROCESSING SYSTEMS AND METHODS

CROSS-REFERENCE TO RELATED APPLICATIONS

This application is a continuation of U.S. application Ser. No. 15/498,048, which was filed 26 Apr. 2017, and which claims the benefit of priority to U.S. Provisional Application No. 62/327,994, which was filed 26 Apr. 2016. The entire disclosures of these applications are incorporated herein by reference.

FIELD

The field relates to medical data processing.

BACKGROUND

Consumers provide feedback through a wide variety of channels, such as social media, vendor websites, vendor call centers, mobile applications, and online stores for mobile applications. The feedback typically is not centrally available, and may be in a wide variety of formats, syntaxes, etc. Additionally, different consumers may use different words or phrases to provide feedback regarding the same topic.

Consumer feedback can be valuable for a vendor to track and analyze to identify specific or widespread issues with products or services provided by the vendor. Due to the different sources of feedback providing the data in an unstructured manner and/or different consumers using different words or phrases to explain the same feedback, analysis of the consumer feedback can be difficult and/or time consuming.

Additionally, in the context of vendors in the medical industry, the information associated with consumers in providing the feedback may be confidential and/or otherwise protected from widespread examination by different persons at the vendor. For example, a customer of a pharmacy benefits manager can provide feedback describing problems or dissatisfaction in a customer experience in attempting to refill a prescription. The identity of the customer, the medication sought to be obtained through the prescription refill attempt, and/or other information may be collected in obtaining the feedback. But, some or all this information may be confidential information that is legally prohibited from being examined by many people at the vendor.

BRIEF SUMMARY

In one embodiment, a method includes obtaining (via a network) source data containing at least one instance of confidential information from a plurality of data sources, determining at least one phrase of interest in the source data, determining at least one of an increase or a decrease in a frequency at which the phrase of interest appears in the source data over time, and detecting (using a data manager device) the confidential information among the source data. The confidential information is prohibited from dissemination to a user of the data manager device that is examining the increase or the decrease in the frequency at which the phrase of interest appears in the source data over time. The method also includes performing (using the data manager device) data substitution to transform the source data into modified data by replacing the detected confidential information in the modified data with at least one contextual placeholder. The substitution of the confidential information with the contextual placeholder allows for the increase or the decrease in the frequency at which the phrase of interest appears in the source data to be determined and presented to the user without revealing the confidential information and without removing context of the source data with the confidential information being substituted. The method also includes generating (using the data manager device) at least one interface respectively reflecting the at least one of the increase or the decrease in the frequency.

In one embodiment, a system includes a data manager device configured to obtain source data from a plurality of data sources via a network. The source data contains at least one instance of confidential information. The data manager device also is configured to determine at least one phrase of interest in the source data and at least one of an increase or a decrease in a frequency at which the phrase of interest appears in the source data over time. The data manager device also is configured to detect the confidential information among the source data, where the confidential information is prohibited from dissemination to a user of the data manager device that is examining the increase or the decrease in the frequency at which the phrase of interest appears in the source data over time. The data manager device also is configured to perform data substitution to transform the source data into modified data by replacing the detected confidential information in the modified data with at least one contextual placeholder, where the substitution of the confidential information with the contextual placeholder allows for the increase or the decrease in the frequency at which the phrase of interest appears in the source data to be determined and presented to the user without revealing the confidential information and without removing context of the source data with the confidential information being substituted. The data manager device also is configured to generate at least one interface respectively reflecting the feedback trend.

In one embodiment, a method includes identifying confidential information in feedback data obtained from different data sources via one or more networks with a data manager device, transforming the feedback data into modified data with the data manager device by replacing the confidential information in the feedback data with different contextual placeholders that define different categories of information without revealing the confidential information, identifying one or more trends in the feedback data using the data manager device; and notifying an operator of the one or more trends in the feedback data without revealing the confidential information to the operator.

DETAILED DESCRIPTION

Figure 1:
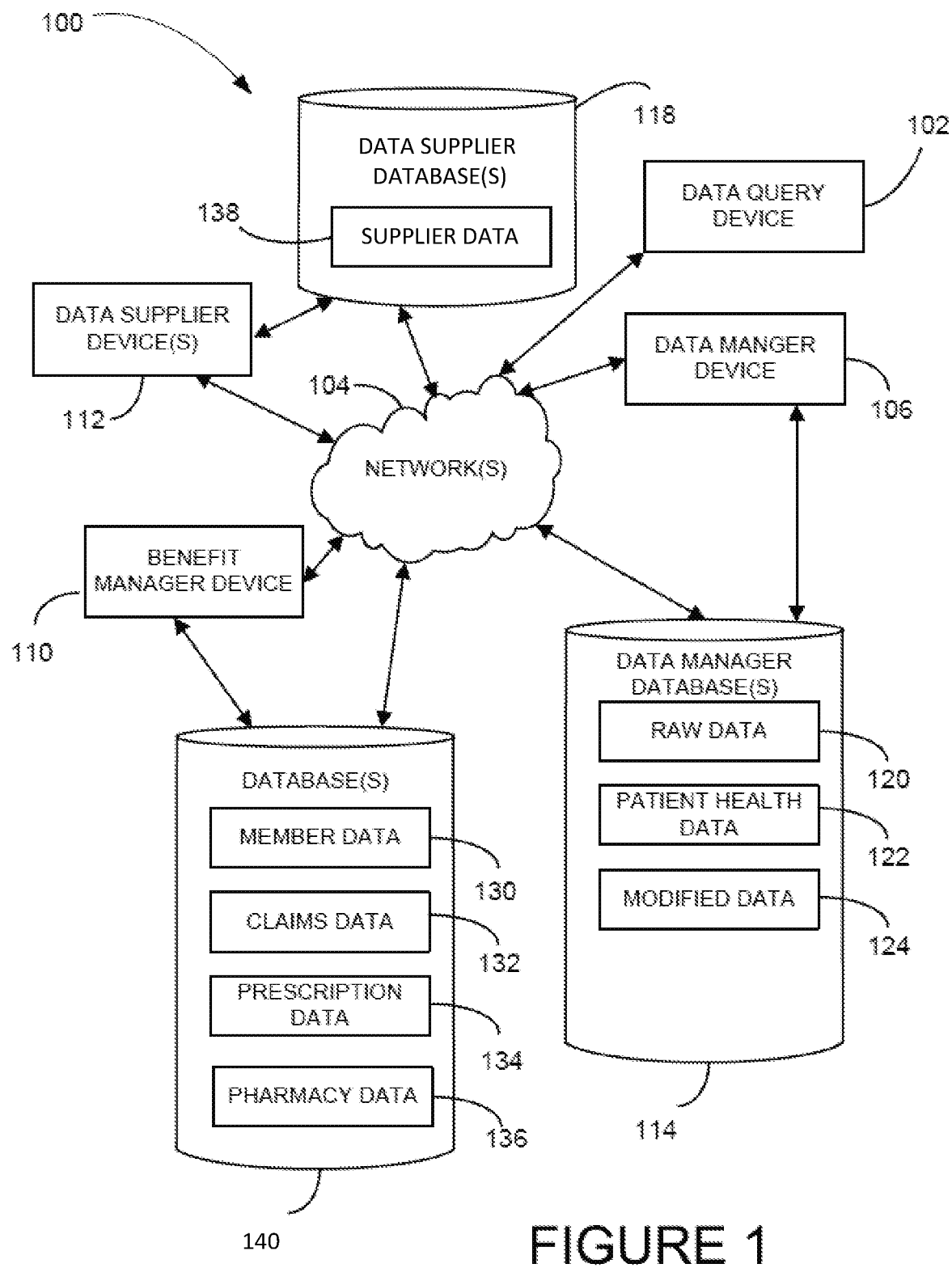
FIG. 1 illustrates one embodiment of a medical processing system.

Example methods and systems for medical data processing are described. The processing allows for data that includes feedback provided by others to be automatically analyzed for identifying common or widespread issues with products or services. Some of the data can include confidential information. The confidential information can be legally and/or contractually restricted from public dissemination, or restricted from dissemination to one or more persons or entities. Examples of confidential information include patient name, drug names, medical diagnoses, addresses, phone numbers, financial information, etc.

The systems and methods can automatically obtain feedback data that includes confidential information and create a modified copy of the feedback data that includes the feedback from customers without the confidential information being viewable. This can permit analysis of the feedback without violating legal or contractual restrictions on dissemination of the confidential information. The original or unmodified version of the feedback data can be transformed into a modified version that replaces confidential information with contextual placeholders.

The contextual placeholders indicate the type or category of confidential information that is removed without revealing specific details about the confidential information. For example, the contextual placeholders can indicate to a reader of the modified data that a person's name was removed from the feedback without revealing the name. Use of the contextual placeholders deidentifies the confidential information from the feedback data by changing certain designated terms (e.g., words, phrases, numbers, and/or dates) to the more generic contextual placeholders. The terms can be changed to still provide meaning or context to the information, while protecting confidential aspects of the data from disclosure. For example, the name of a customer can be replaced with the contextual placeholder [NAME], the birthdate of a customer can be replaced with the contextual placeholder [DATE], and so on. This can allow for the feedback data in the modified data to still provide meaning to users of the systems and methods described herein without revealing confidential information.

The different versions of the feedback data can be accessed by different users based on access levels of the users. Some users can be associated with a higher access level that grants the users with the ability to see the confidential information in the feedback data, while lower access levels can grant users associated with the respective levels the ability to see the feedback data with the confidential information removed. Some access levels may prevent users from viewing any of the feedback information, or fewer portions of the feedback data.

The systems and methods described herein can process or otherwise analyze the information to identify trends in certain themes expressed in the feedback data. For example, feedback from different customers, employees, and/or sources that express or reflect a common complaint about the same product or service can be grouped together. The systems and methods can automatically identify common themes expressed by the feedback, even if different customers, employees, and/or sources of the information use different words, phrases, spellings, data formats, etc., to express the same or similar complaint. This can prevent different expressions of the same feedback from being recognized as different concepts, and alternatively can prevent diametrically opposite expressions from being grouped together as expressing the same theme, as described below (e.g., this can prevent feedback of "good" from being confused with "not good").

At least one technical effect of the subject matter described herein automatically identifies common or widespread complaints or problems based on unstructured data containing customer feedback from a variety of different sources, without revealing confidential information but while providing meaning to the confidential information that is removed. This can allow for users of the systems and methods to quickly and accurately identify and fix problems with computer systems, websites, or the like.

FIG. 1 illustrates one embodiment of a medical processing system 100. The system 100 is an example embodiment in which data integration and modification of feedback data that includes confidential information can be performed. The system 100 includes a data query device 102 in communication with a data manager device 106 over or via a network 104. As described below, the data manager device 106 controls feedback information supplied or otherwise obtained from one or more sources of the feedback. These sources can include data supplier devices 112, data supplier databases 118, benefit manager devices 110, and/or databases 140 of the benefit manager devices 110. The data manager device 106 can obtain source data (that represents consumer feedback) from one or more of these sources via the network 104. As described below, the data manager device 106 can combine and partially modify the source data to remove the confidential information for automated identification of trends in the feedback.

At least some of the source data can be obtained from the data supplier devices 112 and/or the database(s) 118 of the data supplier devices 112. This source data also can be referred to as supplier data 138. Examples of the data supplier device(s) 112 include client support centers, customer call centers, message centers, mobile application stores, email servers, text messaging servers, chat room servers, social media website servers, and the like.

Another data supplier device 112 can include the benefit manager device 110. The benefit manager device 110 represents one or more than one device that is operated by an entity at least partially responsible for the management of a drug and/or medical benefit program. While the entity operating the benefit manager device 110 is typically a pharmacy benefits manager, other entities may operate the benefit manager device 110 either on behalf of themselves, the pharmacy benefits manager, or another entity. In some embodiments, the benefit manager that provides the drug benefit may also provide one or more than one additional benefits including a health benefit, a dental benefit, a vision benefit, a wellness benefit, a radiology benefit, a pet care benefit, an insurance benefit, a long-term care benefit, a nursing home benefit, and the like. The source data provided by or otherwise obtained from the benefit manager device 110 can be referred to as benefit data.

The benefit manager device 110 may provide certain member data 130, claims data 132, prescription data 134, and/or pharmacy data 136 from the database 140 for storage in the database 114 as part of the source data 120. The member data 130 may include information regarding members of a pharmacy benefit plan and/or patients of one, or more than one, pharmacy. The member population may be for a single pharmacy benefit plan (e.g., offered on behalf of a single company), or may for multiple pharmacy benefit plans. In general, the member data 130 may include member name, member contact information (e.g., address, telephone number, email address, and the like), and a client identifier that identifies the client associated with the member and/or a member identifier that identifies the member to the client. Various information in database 114 may be restricted patient health information, e.g., names, dates, drug names, addresses, telephone numbers, and the like.

The claims data 132 includes information regarding pharmacy claims adjudicated by the pharmacy benefit manager under a drug benefit program provided by the pharmacy benefit manager for one, or more than one, clients. In general, the claims data 132 may include client data (e.g., including an identification of the client that sponsors the drug benefit program under which the claim is made, company name, company address, contact name, contact telephone number, contact email address, and the like), an identification of the member that purchased the prescription drug giving rise to the claim, the prescription drug that was filled by the pharmacy (e.g., the national drug code number), the dispensing date, generic indicator, number, medication class, the cost of the prescription drug provided under the drug benefit program, the copay/coinsurance amount, rebate information, and/or member eligibility. The claims data 132 may also include claims adjudicated for healthcare related services other than prescriptions filled under a drug benefit program. Examples of other healthcare related services may include medical services (such as treatment, screening services, laboratory services and the like), dental related services, and vision care related services. Additional information may be included in the various claims of the claims data 132. Various information in the claims data 132 may be restricted patient health information, e.g., names, dates, drug names, medical services, amounts, pharmacy information, and the like.

The prescription data 134 may include information regarding prescriptions that may be issued by providers on behalf of patients, who may be members of the drug benefit plan, for example to be filled by a pharmacy. Examples of the prescription data 134 include patient names, medication or treatment (such as lab tests), dosing information, and the like. The prescriptions may be electronic prescriptions, paper prescriptions that have been scanned, or otherwise turned into data that can be stored in an electronic database as described herein. In some embodiments, the dosing information reflects a frequency of use (e.g., once a day, twice a day, before each meal, etc.) and a duration of use (e.g., a few days, a week, a few weeks, a month, etc.). Various information in the prescription data 134 may be restricted patient health information, e.g., names, dates, drug names, dosage, test results, medical services, amounts, pharmacy information, and the like.

The pharmacy data 136 may include information regarding pharmacies. The pharmacy data may include, by way of example, national provider identifier information associated with the pharmacies, location data regarding the location of the pharmacies, information data regarding the pharmacy hours and/or telephone number, pharmacy network association data defining the pharmacy network associations of which the pharmacies are associated, and the like. Various information in the pharmacy data 136 may be restricted patient health information, e.g., pharmacy information, and the like.

The supplier data 138 as may be stored in the database 118 may include the member data 130, the claims data 132, clinical data, provider data, drug data, the prescription data 134, and/or the pharmacy data 136. The member data 130 and the claims data 132 may be for a same member population as maintained by the benefit manager operating the benefit manager device 110, or for a different population. In some embodiments, the source data 120 is stored separately from the member data 130, claims data 132, and/or supplier data 138. Various information in the supplier data 138 may be restricted patient health information.

The clinical data may include clinical records regarding member diagnosis and/or therapy. The clinical data may be obtained from hospitals, medical insurance companies, drug trials, medical laboratories in the form of clinical records and/or the member via online questionnaires, for example. In some embodiments, the clinical data includes medical claims and/or lab data. In some embodiments, the clinical data includes medication data (e.g., for a claim made under the medical benefit instead of the prescription drug benefit). Various information in the clinical data may be restricted patient health information, i.e., information that must be removed or redacted to comply with medical data rules, regulations and laws.

The devices 102, 106, 110, 112 represent hardware circuitry that includes and/or is connected with one or more than one processor, such as one or more than one microprocessor, field programmable gate array, integrated circuit, or the like. Examples of the devices 102, 106, 110, 112 include a set-top box (STB), a receiver card, a mobile telephone, a personal digital assistant (PDA), a display device, a portable gaming unit, and a computing system; however other devices may also be used. For example, the devices 102, 106, 110, 112 may include a mobile electronic device, such an IPHONE or IPAD device by Apple, Inc., mobile electronic devices powered by ANDROID by Google, Inc., and a BLACKBERRY device by Blackberry Limited. The devices 102, 106, 110, 112 may also include other computing devices, such as desktop computing devices, notebook computing devices, netbook computing devices, gaming devices, and the like. Other types of electronic devices may also be used. When instructions for the present methods are loaded into one or more of the example systems, the device 102, 106, 110, or 112 is specifically dedicated to the present disclosure. Other circuitry may also perform that present methods.

The network 104, by which one or more than one of the devices 102, 106, 110, 112 communicate, can include one or more than one computerized communication network. Examples of the network 104 include a Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 can also include optical communications. Other wired and wireless networks may also be used. In some embodiments, the network 104 can include proprietary network communication technologies such as secure socket layers (SSL) technology, technology found in a prescribing network (e.g., the electronic prescribing network operated by Surescripts of Arlington, Virginia), and the like.

The network 104 can be at least partially outside of restrictions on confidential information contained in the data described herein. For example, some networks can include restrictions on which users are able to communicate and/or view confidential information sent via the networks. These restrictions can include limitations on which users have legal or regulatory permission to send or receive the confidential information via the networks. Other networks do not include such restrictions. For example, networks that form at least part of the publicly available Internet may not include restrictions on who can send data within the network. In one embodiment, at least part of the network 104 is outside of restrictions on who can send or receive data. But, the feedback information can still be communicated for viewing and/or analysis via such a part of the network 104 due to the confidential information being removed from the data, as described herein.

Figure 2:
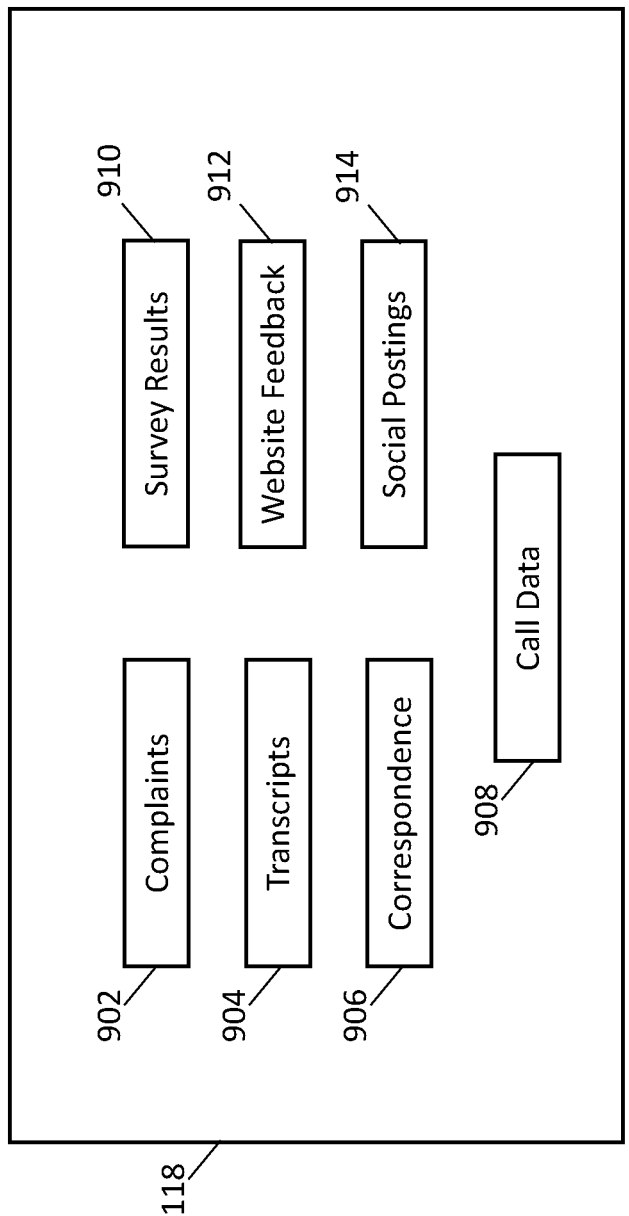
FIG. 2 illustrates one example of a database shown in FIG. 1 that can be maintained by a source of source data.

FIG. 2 illustrates one example of the database 118 that can be maintained by a source of the source data. The database 118 can store one or more types of source data that is accessible by the data supplier devices 112 for communication to the data manger device 106 via the network 104. The database 118 can store a variety of information that represents feedback concerning services, products, experiences, or the like. Examples of the source data include complaint data 902 ("Complaints" in FIG. 2), which can represent recorded information on internal employee complaints or feedback, such as emails, surveys, completed website forms, or the like, through which employees can provide complaints regarding company services or the like. Another example of source data is transcript data 904 ("Transcripts" in FIG. 2), which represents written transcriptions of verbally communicated information. Examples of the transcript data 904 include transcripts of telephone calls pharmacy benefit manager or another entity, transcripts of chat sessions, etc. Another example of source data is correspondence data 906 ("Correspondence" in FIG. 2), which represents written correspondence to or from one or more persons. Examples of the correspondence data 906 include emails, text messages, scanned copies of hardcopy correspondence, or other electronic correspondence.

Another example of source data is call data 908, such as dates and/or times of phone calls, phone numbers, area codes (without the remainder of the phone number), or the like, associated with received phone calls. Survey results 910 represents another example of source data, and can include patient satisfaction data regarding various programs and services offered by the pharmacy benefit manager or other supplier. The patient or member may be asked about their use of and satisfaction with a specific service, e.g., home delivery, member services, participating pharmacy program, and/or a specialty pharmacy program. The survey may target a random sample of members who have filled a prescription, used received medical treatment, or contacted a contact center in the prior two weeks. The survey may record their satisfaction on a scale range (e.g., one to five, one to ten, or the like). There are multiple sub-sources that may use the survey, including but not limited to, a call/contact center, home delivery pharmacy, retail pharmacy, and specialty pharmacy. Another survey may be an employee feedback on aspects of home delivery, from placing their order, communications they received and interactions they had with the home delivery team.

Another example of source data is website feedback 912, which represents data indicative of user feedback provided to websites, user rankings of websites, and the like. This data may be obtained from a mobile app store, the website itself, the hosting service of the website, etc. The source data can include social media posts 914 ("Social Postings" in FIG. 2). This data can include postings on one or more social media websites or mobile apps that are accessible. For example, the social media posts 914 can be postings on FACEBOOK, TWITTER, LINKEDIN, or the like, that refer to the pharmacy benefit manager or another entity.

The source data can be updated over a first time period or other time period. This data may be stored in a database 120. The data may also include information relating to escalation(s) to senior management within the company or pharmacy benefit manager. The escalations data is typically worked by a small team where the team works to resolve a concern of a patient, identify a root cause or opportunity, and ensure that solutions are in place to avoid future occurrences of the concern.

The data may also include social media data. The specialty social media teams and systems monitor social media, e.g., FACEBOOK, TWITTER, CONSUMER AFFAIRS, blogs, forums and YELP, to develop and input social media data into the databases. Such social media data may also develop complaint requests to the escalation team or compliments to the escalations team. Other types of input may be email, voicemail, and calls from a member. The data may be website feedback. The website feedback may be input into a device by a member via a member website (e.g., at www.express-scripts.com), e.g., at a "tell us about your experience" link, which may be part of a "Contact Us" page. A patient or member provides their net promoter score on how likely the patient or member is to recommend EXPRESS SCRIPTS to friends and family and provide comments related to their score.

Optionally, the source data (e.g., the benefit data) can include information regarding prescribers, pharmaceutical manufacturers, prescription drugs, prescription drug average wholesale price, co-pays, clients of a pharmacy benefits manager, and the like. In some embodiments, the source data can be developed through analysis performed by the data supplier device 112 or by a person or organization that operates the data supplier device 112. In some embodiments, the source data may be developed by a single organization, or multiple organizations, and provided to the data supplier device 112. The source data 138 developed or obtained by the data supplier device 112 need not be related to prescription drugs, but can be from one, or more than one, data categories of interest to the data manager device 106. In some embodiments, the data supplier operating the data supplier device 112 is a client of the pharmacy benefits manager operating the benefit manager device 110 and/or a client of the data manager operating the data manager device 106. In some embodiments, the data supplier operating the data supplier device 112 is a governmental organization. In an example, the data from the data supplier device 112 may also be data that is restricted from sharing outside a protected health data secure or compliant system or device.

The data can be updated by different sources at different rates or frequencies. For example, some sources of the feedback can be updated in real time (e.g., the feedback at the data manager device 106 is updated as new feedback is received) or at different rates or frequencies by different sources (e.g., one source updates every hour, another source updates every day, and another source updates every week).

The source data can include confidential information that may not be disclosed to some entities or persons due to legal and/or contractual restrictions. Examples of confidential information include patient health information (such as medication name, brand name, generic name, therapy class, prescription drug average wholesale price, medical conditions, and/or medical diagnoses), names, dates, social security numbers, financial transaction numbers or accounts (e.g., credit card numbers), data attributes for many healthcare providers (such as healthcare provider name, healthcare provider address, healthcare provider professional affiliations, or healthcare provider number), member information (such as member address, member date of birth, or healthcare plan identification number), pharmacies (such as pharmacy name, pharmacy address, or pharmacy number), and the like. Some laws or regulations can restrict which persons are allowed to view medical information (e.g., caregivers or persons previously identified by a patient), with other persons not being allowed to view the information.

The data manager device 106 can examine the source data to determine whether the source data includes confidential information. This examination can be performed by the data manager device 106 parsing the information in the source data by breaking apart the source data into different parts of sentences (e.g., object words, verbs, nouns, subject words, adjectives, adverbs, etc.), and comparing the parsed information to one or more than one list, table, or other memory structure containing designated confidential information. The designated confidential information can be words, phrases, numbers, dates, etc., that are previously identified and labeled as confidential information. For example, a list of various given names, last names, medical conditions, medications, dates, or the like, can be used to by the data manager device 106 to identify confidential information. If a word or phrase appearing in the source data matches or is similar to the identified confidential information, then the word or phrase is identified by the data manager device 106 to be confidential information.

Optionally, if a format or syntax of a word or phrase in the source data is the same or similar to a format or syntax designated as confidential information, then the word or phrase is identified as confidential information. For example, source data that includes a month that is within a designated number of characters (e.g., ten characters) of a number can be identified as a date (which is confidential information). A sequence of numbers can be identified by the data manager device 106 as confidential financial information (e.g., social security numbers, credit card numbers, etc.). A word or phrase in the source data can be identified by the data manager device 106 as confidential patient health information when the word or phrase is the same as or similar to one or more than one medications, medical conditions, and/or diagnoses previously identified as confidential information.

Responsive to identifying confidential information in the source data, the data manager device 106 can create a modified version of the source data that does not include the confidential information. This version of the source data can be referred to as modified data. The modified data can include the non-confidential information and contextual placeholders in place of the confidential information.

As described above, a contextual placeholder is a label of a category or type of confidential information that does not disclose the specific details of the confidential information. For example, [NAME] can be used as a contextual placeholder in the modified data to replace a customer's name, [DATE] can be used as a contextual placeholder in the modified data to replace a date, [MEDICAL INFO] can be used as a contextual placeholder in the modified data to replace a medical condition, medication, or medical diagnosis, [CLIENT NAME] can be used as a contextual placeholder in the modified data to replace the name of a client of a pharmacy benefit manager, [FINANCIAL INFO] can be used as a contextual placeholder in the modified data to replace an account number, social security number, bank name, or the like.

Replacing the confidential information with contextual placeholders can allow a viewer of the modified data to determine additional information about the feedback represented by the modified data, without revealing the details of the confidential information. In one example, the confidential information that is replaced with contextual placeholders is that data that falls under or within disclosure restrictions of the Health Insurance Portability and Accountability Act. For example, the source data can include a customer entry of the following feedback: "I am Jackson Ryan. I am a diabetic who tried to buy insulin at EJ Pharmacy yesterday using my debit card and it won't work." The data manager device 106 determines that the terms "Jackson Ryan", "a diabetic," "insulin", "EJ Pharmacy", "yesterday", and "debit card" are confidential information. The data manager device 106 can create the modified data by replacing "Jackson Ryan" with the contextual placeholder [NAME], "diabetic" with the contextual placeholder [MEDICAL CONDITION], "insulin" with the contextual placeholder [MEDICAL INFO], "EJ Pharmacy" with the contextual placeholder [CLIENT NAME], "yesterday" with the contextual placeholder [DATE], and "my debit card" with the contextual placeholder [FINANCIAL INFO]. The resulting modified data is then: "I am [NAME]. I am [MEDICAL CONDITION] and I tried to buy [MEDICAL INFO] at [CLIENT NAME] [DATE] using [FINANCIAL INFO] and it won't work."

The contextual placeholders are different from each other so that a reader or computerized analysis of the contextual placeholders in combination with the other information in the data is able to determine the context or theme of the feedback. The modified version of the source data provides the reader with enough context to determine the theme of the complaint of the source data without revealing any confidential information. For example, a reader of the modified data can still determine that the customer attempted to purchase some medical product or service and encountered an issue.

In contrast, replacing all confidential information with the same or similar placeholders could muddle or confuse the theme of the feedback. With respect to the preceding example, replacing the confidential information with X's can confuse the theme of the feedback: "I am XXXXX. I am XXXXXXX and I tried to buy XXXXX at XXXXX XXXXX using XXXXX and it won't work." It is unclear to the reader whether this feedback is complaining that the customer was unable to purchase medication or another product, whether the customer is stating that the attempted purchase was at an identified location, date, and/or time, and/or what the customer attempted to use to make the purchase. For example, it is unclear if the customer is complaining that he or she was unable to use the front door of a pharmacy, the drive through of the pharmacy, the customer's debit card, or the like, to complete the purchase.

The removal of confidential information from data, while maintaining the overall theme of the customer expression represented by the data, can be a problem that is unique to computerized networks that collect the confidential information. For example, in response to a dissatisfied experience with a pharmacy benefit manager or client (e.g., pharmacy) of a pharmacy benefit manager, persons providing feedback may include confidential information. Computerized systems can be used to record this feedback, and these systems usually store the feedback as the feedback is provided. That is, the feedback containing confidential information is stored by these systems with the confidential information remaining in the feedback. Simply searching for and removing those terms in the data that reflect confidential information can result in nonsensical feedback being represented by the data. But, replacing the confidential information with contextual placeholders in the created copy of the data can allow the inventive systems and methods described herein to analyze the feedback and/or provide the feedback for review by others without losing context or significant meaning from the feedback.

The data manager device 106 can store the source data from the supplier devices 112 and/or benefit manager device 110 in a database 114 as raw data 120. A copy of the raw data 120 that includes the confidential information can be stored in the database 114 as patient health data 122. Optionally, the copy of the raw data 120 that includes confidential information, but not necessarily confidential patient health data, can be stored in the database 114 as confidential data 122. The modified or deidentified data having the confidential information replaced with the contextual placeholders can be stored by the data manager device 106 in the database 114 as modified data 124.

Figure 3:
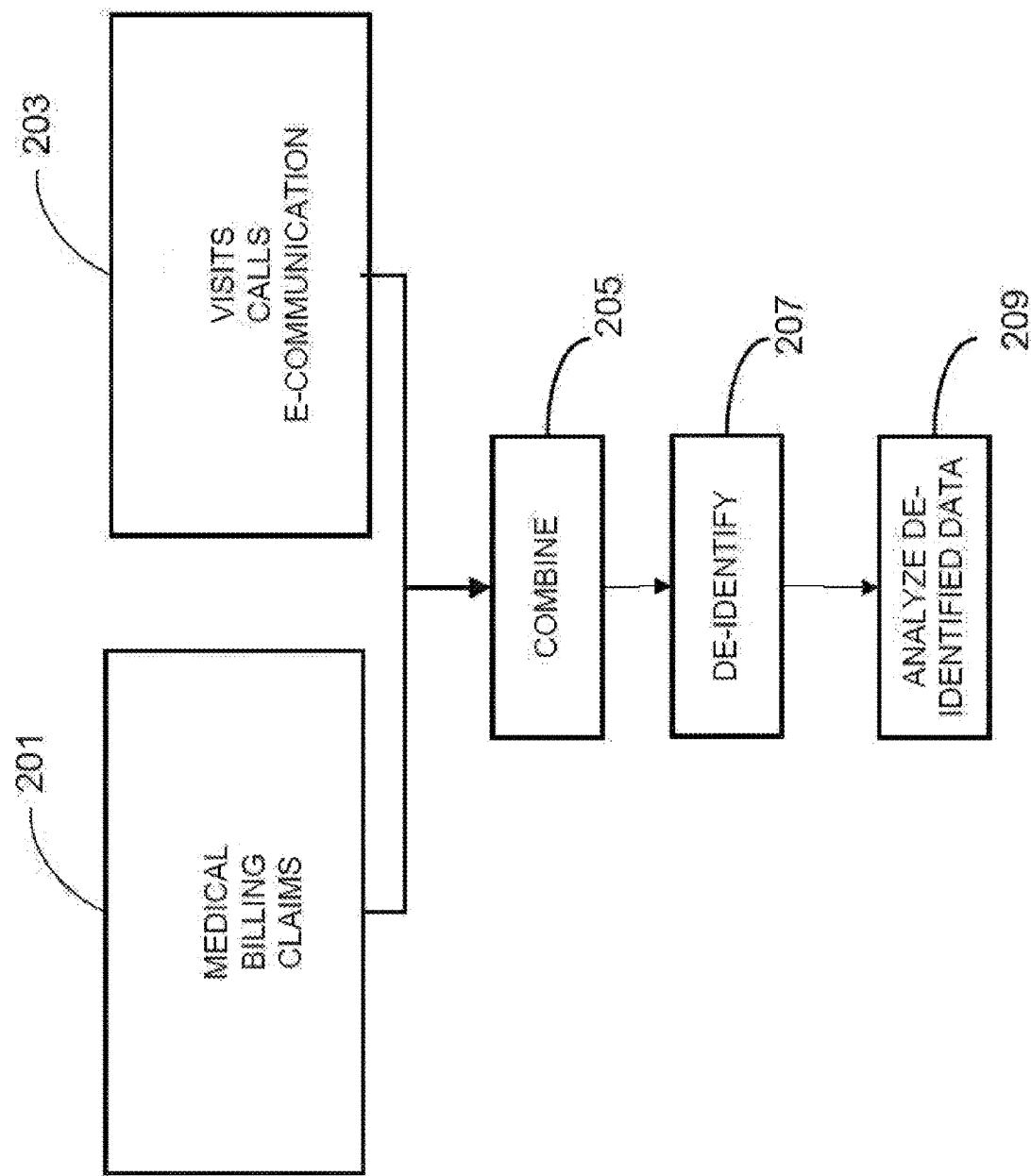
FIG. 3 schematically shows how source data and modified data are created in one example.

FIG. 3 schematically shows how the source data 120 and the modified data 124 are created in one example. Databases 201 may include medical records, billing records, and/or claims data. The databases 201 can represent at least some of the data 120, 124 stored in the database 114. A patient communication database 203 may include electronic text that represents interaction of a member with the company, e.g., a pharmacy benefit manager, and may include call data, in-person visits, website visits, and e-communication(s). The database 203 can represent at least some of the supplier data 138 stored in the database 118. Databases 201, 203 may include protected health information or other confidential information. A device 205 (e.g., the data manager device 106) combines the data from the databases 201, 203 to provide a comprehensive database (e.g., the source data 120) in the database 114. The device 205 may de-identify the combined data by replacing the confidential information with contextual placeholders so that the data can be shared outside the restrictions of protected health information rules, regulations, and laws. An analyzing device 209 (e.g., the data manager device 106) may perform analysis of the de-identified data, as described herein.

The database 203 may also include social media data. Social media data can include data from the social media accounts of the medical care provider or company. The social media data may be acquired by using programs to routinely search for key words, e.g., the company name, drug names, illness information. Social media may include data posted to electronic hosts, Twitter, Facebook, websites and the like. Posts to regulatory agencies or reviewing sites may also be downloaded to the database 203. In an example, this data is automatically downloaded and then may be reviewed for content. In an example, a team of devices, e.g., manned by trained data reviewers, reviews the online data and downloads or inputs relevant data to the database 203. In some instances, the data can be linked to a specific user or member.

Figure 4:
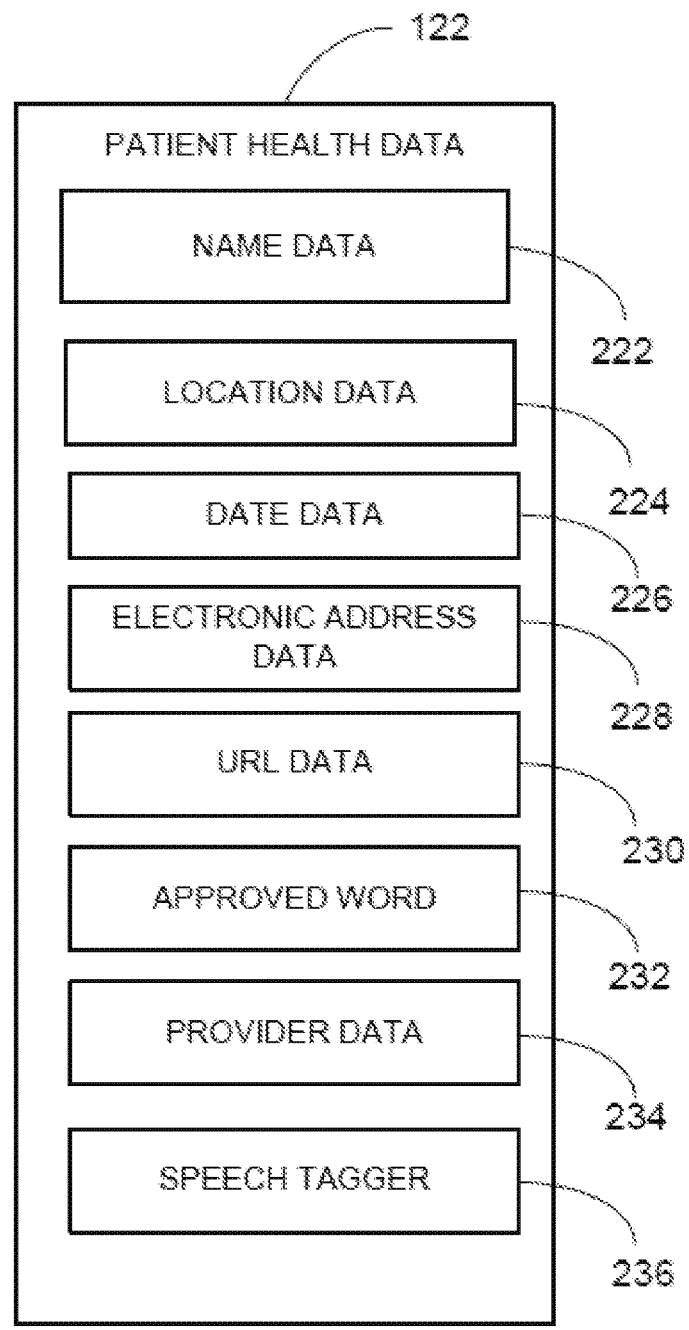
FIG. 4 shows a schematic view of patient health data that represents confidential information.

FIG. 4 shows a schematic view of the patient health data 122 that represents confidential information. A name database 222 is stored in the database 114 and can be used to identify names that are in the source data 120. The name information in the name database may be used to replace names with a contextual placeholder, such as a name indicator, to produce the modified data 124. The name database 222 may store a list of names of members of a pharmacy benefit plan in one embodiment. The name database 222 optionally includes a listing of all common names that may be used. The name database 222 may include names of medical providers, e.g., doctors, nurses, clinicians, etc. In one embodiment, the names in the source data 120 that appear in the name database 222 can be substituted in the modified data 124 with a contextual placeholder such as [NAME], [FIRST NAME], [PROPER NAME], [LAST NAME], [SURNAME], [MIDDLE NAME], or the like.

A location database 224 is stored in the database 114 and can be used to identify locations that are in the source data 120. The location information in the location database 224 can be used to replace location information in the master data 120 with contextual placeholder (e.g., a location indicator) to produce the modified data 124. The location database 224 can include street names and names of clinics and medical providing institutions. In one embodiment, the locations in the source data 120 that appear in the location database 224 can be substituted in the modified data 124 with a contextual placeholder such as [ADDRESS], [MAILING ADDRESS], [PHYSICAL ADDRESS], [CITY], [TOWN], [STATE], [ZIP CODE], [COUNTY], [COUNTRY], [CLINIC], [HOSPITAL], or the like.

A date database 226 is stored in the database 114 and can be used to identify dates that are in the source data 120. The date information of the date database 226 can be used to replace dates in the source data 120 with a contextual placeholder (e.g., a date indicia or indicium) to produce the modified data 124. The date database 224 can include various forms of dates, e.g., dd/mm/YYYY; mm/dd/YYYY; YYYY/mm/dd; or fully written months, days, and year or combinations thereof. In these examples, dd represents a date; mm represents a month; and YYYY represents a year. In an example, the date database may include algorithms to search electronic data to remove dates from the source data 120. In one embodiment, the dates in the source data 120 that have a format appearing in the date database 226 can be substituted in the modified data 124 with a contextual placeholder such as [DATE], [MONTH], [WEEK], [DAY], [YEAR], [TIME], [HOUR], [MINUTES], [SECONDS], or the like An electronic address database 228 is stored in the database 114. The electronic address data in the electronic address database 228 can be used to identify electronic addresses that are in the master data 120 and to replace the electronic address replaced using electronic address indicia to produce modified data 124. Examples of electronic addresses can be email addresses, twitter handles, online names, social networking names, and the like. In one embodiment, the electronic addresses in the source data 120 that appear in the electronic address database 228 can be substituted in the modified data 124 with a contextual placeholder such as [EMAIL ADDRESS], [TWITTER ADDRESS], [FACEBOOK NAME], [ELECTRONIC ADDRESS], [SOCIAL MEDIA ADDRESS], [HANDLE], [ONLINE NAME], or the like A uniform resource locator (URL) address database 230 is stored in the database 114. The URL data in the URL database 230 can be used to identify URL information that is in the source data 120 and to replace the URL replaced using a URL indicia to produce modified data 124. In one embodiment, the URL in the source data 120 that appear in the URL address database 230 can be substituted in the modified data 124 with a contextual placeholder such as [URL], [WEBSITE], [WEBSITE ADDRESS], or the like An approved word database 232 can be stored in the database 114. The approved word database 232 can include words that are not protected health information or that are not confidential information. Accordingly, the words in the approved word database 232 can be passed from the source data 120 to the modified data 124 without modification, redaction or replacement.

A speech tagger 236 can be stored in the database 114 and can be used to identify parts of speech in the source data 120. Certain parts of speech, e.g., articles and prepositions need not be removed from the source data 120 to create the modified data 124. The speech tagger 236 can be run on the source data 120 first and the other data preparation steps need only operate on the parts of speech that are patient identifiers, e.g., nouns and verbs. This will improve the processing speed and accuracy of cleansing the source data 120 of protected health information to produce modified data 124 that is compliance with disclosure of protected health information.

A provider database 234 is stored in the database 114 and can be used to identify providers that are in the source data 120 and replaced using a provider indicator to produce modified data 124. The provider data 234 may include information regarding prescribers and/or providers of healthcare services. The provider data may include, by way of example, provider name, national provider identifier information associated with the providers, location data regarding the location of the providers, information data regarding the provider hours and/or telephone number, provider network association data defining the provider network associations of which the providers are associated, business relations with other providers, services provided by the provider (e.g., prescriptions issued by the provider, treatment services administered by the provider, testing services administered by the provider, etc.), and the like. The providers may be at a physician's office, a hospital, a testing laboratory, a pharmacy, a location associated with a pharmacy benefit manager, or the like. In one embodiment, the provider information in the source data 120 that appears in the provider database 234 can be substituted in the modified data 124 with a contextual placeholder such as [PROVIDER], [PROVIDER INFORMATION], or the like.

Returning to the description of the system 100 shown in FIG. 1, in one embodiment, users can be associated with different levels of access to the data. For example, a user can be assigned or otherwise associated with first login credentials that are associated with a first level of access. This first level of access can allow the user to view the raw data 120 (e.g., using a computer or computerized device, such as a mobile phone), the confidential patient health data 122, and the modified data 124. Another user can be assigned or otherwise associated with different, second login credentials that are associated with a different (e.g., lower) second level of access. This second level of access can allow the user to view the modified data 124, but not the raw data 120 or the patient health data 122. The access levels can be assigned by the data manager device 106 to different users (e.g., based on identities of the users, job titles of the users, etc.) to control which users can view confidential information and which users are prevented from viewing confidential information. This can prevent unintentional access to or disclosure of the confidential information.

An operator or user of the data query device 102 can use the data query device 102 to run a data query, or multiple data queries, on the raw data 120 and/or the modified data 124. The query can be run on the data to obtain information of interest to the operator of the query device 102 or to another individual or device. The operator of the data query device 102 may not be approved to view or access confidential information that is regulated and protected patient health information. For example, the access level granted to or associated with the operator may not permit access to or viewing of the confidential information in the modified data 124. But, the data analysis device 102 can perform analysis on the modified data 124, including on the contextual placeholders indicating the confidential information, in response to the query provided by the operator.

Various data analyses can be performed by the data manager device 106 on the modified data 124 received by the data query device 102 in response to a query. For example, business trends, efficiency analysis, fraud analysis, waste analysis, abuse analysis, trends in one or more themes appearing in the restricted data, or the like, can be identified by the data query device 102 examining the modified data 124. For example, if the modified data 124 reflects customer feedback with increases or decreases in complaints about a service, website, pharmacy, product, or the like, the increases or decreases in the complaints can be automatically identified and reported to a user of the system 100. The data query device 102 may output a display with text statistical analysis, e.g., word clouds, topic identification by language analysis, graphs of the results, and the like.

The data query device 102 examines the modified data 124 to provide meaning and context to feedback from multiple different persons and/or sources, and that contains confidential information. For example, the data query device 102 can examine the modified data 124 to determine whether many customers are complaining about a website or mobile application service interruption, whether customers are expressing displeasure with the same call center, whether customers are complaining about the cost of a particular product, whether customers are complaining about the same insurance plan not providing benefit coverage for a particular medication, etc. The feedback provided by different persons via different sources is unstructured data which can include confidential information. Unstructured data can be difficult to examine for analyzing the data. For example, complaints from different persons about a product cost coming from different social media websites, a pharmacy benefit manager website, a mobile application store, and/or a call center can be recorded differently in different data formats and/or syntaxes. Additionally, these complaints can include confidential information.

The data manager device 106 can replace the confidential information with the contextual placeholders, as described above, but the various formats and syntaxes of the complaints can be difficult to effectively identify trends in the complaints. Some systems and methods may examine data for trends by counting how often a designated word is used in the data. Misspellings, use of uncommon phrases or expressions, or the like, can cause some feedback in the modified data 124 to be missed and/or misinterpreted. For example, the modified data 124 can represent negative feedback stating that a new website feature of a pharmacy benefit manager is "not good." Because this feedback includes the word "good," however, some systems and methods may incorrectly identify this feedback as being positive (e.g., expressing satisfaction with the website feature) instead of negative (e.g., expressing dissatisfaction with the website feature).

The data manager device 106 can identify how often contextually related phrases or terms are used in the modified data 124 to identify trends in the feedback. A trend can be identified when dissatisfaction is expressed in feedback at least a designated number of times within a designated time period (e.g., one day, one week, one month, or one year) about the same product, service, feature, or the like. A trend also can be identified when satisfaction is expressed at least a designated number of times within a designated time period about the same product, service, feature, or the like.

The data manager device 106 can determine how often the same theme (e.g., satisfaction or dissatisfaction) is expressed in feedback by counting how often the same or similar multiple word phrases appear in the modified data 124. For example, the data manager device 106 can count how often a negative word (e.g., terrible, stinks, not, no, etc.) is within a designated number of characters or words from the same noun group. Optionally, the data manager device 106 can count how often a positive word (e.g., great, yes, etc.) is within a designated number of characters or words from the same noun group. A noun group can include a single word or a group of words that are designated to be synonyms of each other. As one example, the modified data 124 can include the following feedback:

"The payment page on the Acme website won't work."
"Site not working. I cannot submit payment for my mail order [MEDICATION]."
"This site stinks. It does not take my [FINANCIAL INFO]."
"You really need to fix this payment page. Not good at all."

The data manager device 106 can determine how often a noun group indicative of a website (e.g., the Acme website) is used in the modified data 124. This noun group can be defined by the data manager device 106 (e.g., based on input provided by a user) to include the words "site," "website," "page," "forum," "web site," etc. In one embodiment, the noun group can be defined to include misspellings of these words, such as "ste," "websight," "paeg," "forem," etc.

As described in more detail below, the data manager device 106 examines the modified data 124 to determine how often one or more (or any) of the words in the group appear in the modified data 124. The data manager device 106 also can examine nearby words and phrases in the modified data 124. For example, the data manager device 106 can examine additional words appearing within three words (or another length) of the term of interest (e.g., synonyms for the word website). These additional words can be synonyms and/or common misspellings for positive statements (e.g., "yes," "good," "works," etc.) or synonyms and/or common misspellings for negative statements (e.g., "no," "bad," "fails," etc.). Based on the term of interest and the additional nearby words, the data manager device 106 can identify a theme appearing in the modified data 124.

With respect to the feedback examples provided above, the data manager device 106 can identify the following terms of interest and positive or negative statements:

payment AND page AND website AND won't work
site AND not working AND payment
site AND stinks AND not AND [FINANCIAL INFO]
payment AND page AND not good Each of these groups expresses a common theme in the feedback obtain from disparate sources: dissatisfaction with the payment feature on a website. Searching for isolated words alone would miss or misidentify some of the feedback as expressing this common theme. For example, the feedback "The payment page on the Acme website won't work" could be misinterpreted as expressing a theme that the website will not work, but not the payment feature or page on the website. The feedback "Site not working. I cannot submit payment for my mail order [MEDICATION]" could be misinterpreted as expressing a theme that mail order payment is not working instead of the payment feature or page on the website not working. The feedback "You really need to fix this payment page. Not good at all" could be misinterpreted as the payment page is good instead of "not good."

After identifying the these expressed in the feedback, the data manager device 106 can generate one or more outputs for presentation to a user of the system 100. For example, the data manager device 106 can generate a signal that instructs a display device to display a word cloud, graph, table, or the like, indicative of the term of interest and how often the term of interest appears in the feedback.

Figure 5:
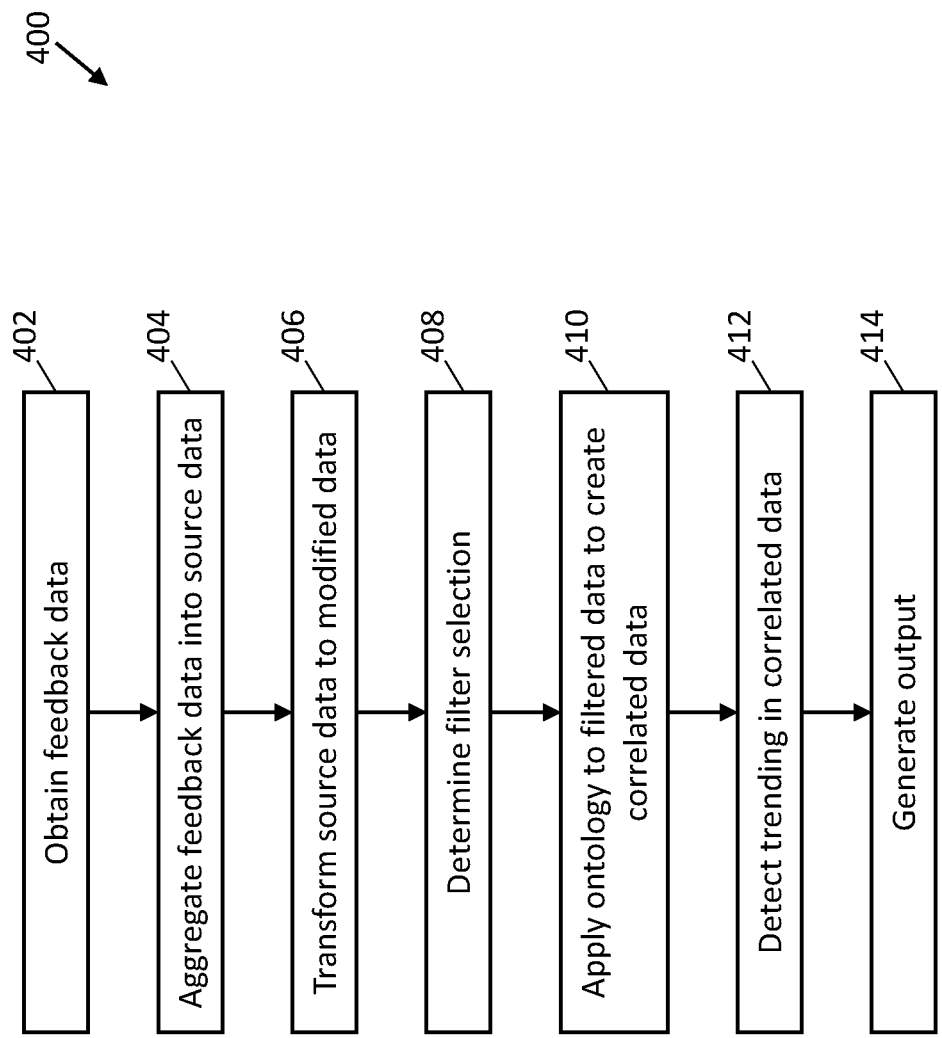
FIG. 5 illustrates a flowchart of a method for analyzing feedback information that includes confidential information.

FIG. 5 illustrates a flowchart of a method 400 for analyzing feedback information that includes confidential information. The flowchart can represent operations performed by the system 100 under the direction of one or more software applications. At 402, feedback data is obtained. The feedback data represents feedback provided by persons such as customers, visitors to websites, or the like, as described above. The feedback data can be obtained from a variety of sources, such as the supplier devices 112 and/or the benefit manager device 110 shown in FIG. 1. In addition to the examples of sources of the feedback data described above, one or more sources of the feedback data can include a client support center that researches and resolves escalated and complex inquiries or complaints related to beneficiary-specific pharmacy benefits and/or a call center that provides call transcriptions via speech analytics. The call transcriptions can be categorized based on a predefined set of words and phrases that have a similar meaning (e.g., synonyms). The call transcriptions can be used to pinpoint specific types of calls and to identify changes in category volume over time. Another example of a source can be an internal human resources department. This department can provide information on employee-submitted complaints due to inaccurate information received from another employee, information on expressed dissatisfaction (orally or in writing) with service being provided by the employer, call transcripts, and the like. Another example of a source can be a website or results of a customer survey. The feedback data can be communicated from the sources to the data manager device 106 via the network 104.

At 404, the feedback data is aggregated into source data. The feedback data can be aggregated by combining the feedback data obtained from each of the sources into a larger memory structure. For example, multiple tables or spreadsheets of the feedback data provided by the multiple sources can be combined into a single table or spreadsheet.

Figure 6:
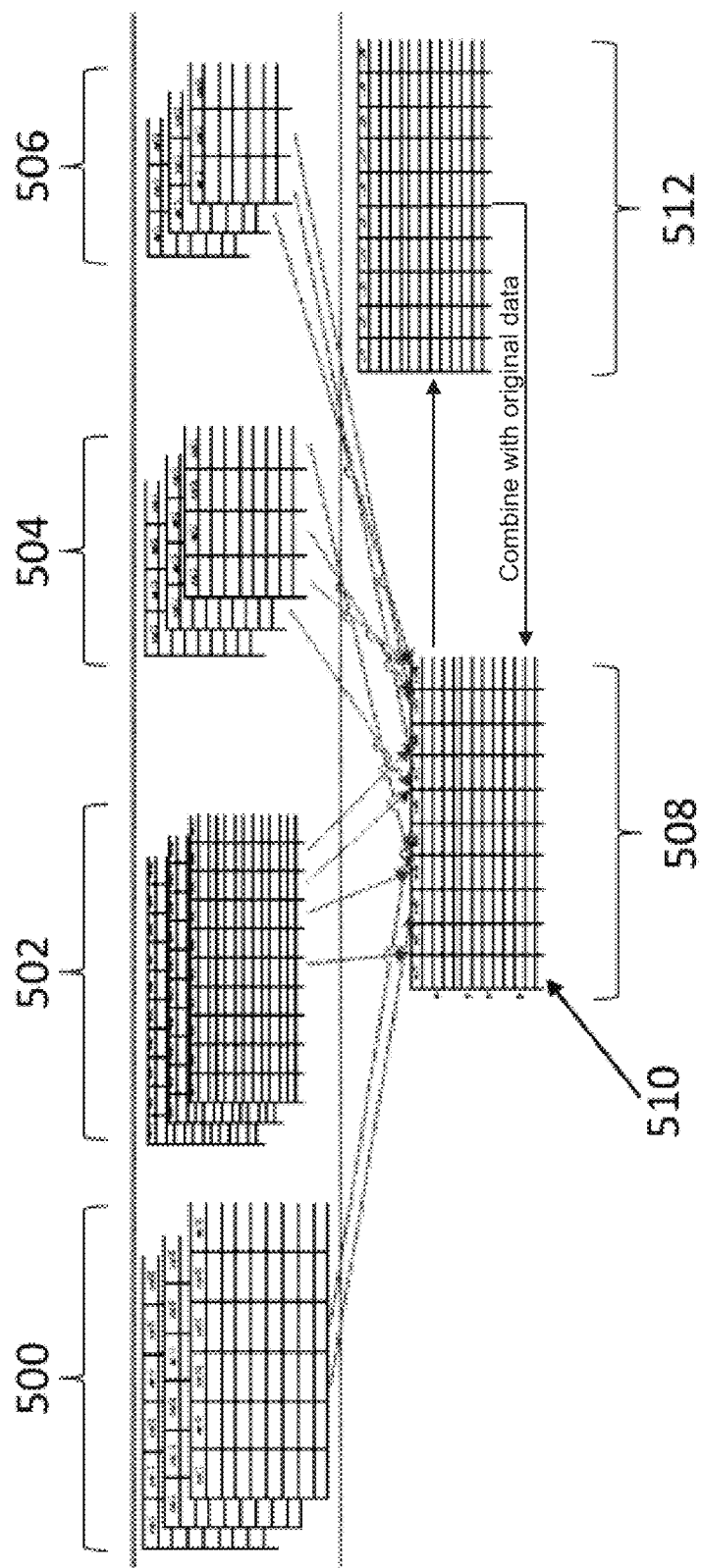
FIG. 6 illustrates one example of aggregating and transforming feedback data.

FIG. 6 illustrates one example of aggregating and transforming feedback data. The feedback data is represented by multiple separate groups of spreadsheets 500, 502, 504, 506, with each group of spreadsheets 500, 502, 504, 506 representing feedback data obtained from a different source. The feedback data contained in the spreadsheets 500, 502, 504, 506 is combined (e.g., by the data manager device 106) into the source data 120, which is represented in FIG. 6 as another spreadsheet 508. The source data 120 can be formed by creating copies of the feedback data in the spreadsheets 500, 502, 504, 506 and inserting the copies of the feedback data into separate columns 510 of the source data spreadsheet 508. This can result in different columns 510 of the source data spreadsheet 508 each representing or including feedback data from a different source, thereby assisting in keeping the unstructured feedback data from each source separate from the unstructured feedback data from other sources while keeping the unstructured feedback data from the same source together.

Returning to the description of the flowchart of the method 400 shown in FIG. 5, at 406, the source data is transformed into the modified data. As shown in FIG. 6, the source data 120 can be transformed by creating a copy 512 of the source data 120 with the confidential information in the source data 120 removed, or at least replaced with contextual placeholders. The confidential information can be removed by the data manager device 106 searching through the source data 120 (e.g., the spreadsheet 508) for names, medications, financial information, dates, addresses, or the like, that are previously identified as confidential information. The data manager device 106 can store (or access from the database 114) lists of words indicative of confidential information and can compare the contents of the source data 120 with the word lists to identify the confidential information. In one embodiment, different word lists are maintained for different types of confidential information (e.g., a list of names, a list of medications, etc.). If the data manager device 106 discovers that confidential information from a word list appears in the source data 120 (or the copy 512 of the source data 120 used to create the modified data 124), then a contextual placeholder associated with the list is used to replace the confidential information. The confidential information can be completely removed from the copy 512 of the source data 120 such that no confidential information remains in the copy 512 of the source data 120. Once the confidential information is removed and replaced by the contextual placeholder, the copy 512 of the source data 120 becomes the modified data 124 described above.

The source data 120 provided by one or more than one source can be updated. For example, a website can provide feedback received by a script running on the site once a day at a designated time, a call center can provide call transcripts as the call transcripts are generated (e.g., in real time), social media sites can be searched for feedback once a day, etc. Different sources may update the feedback data provided by those sources on different schedules. The spreadsheet or spreadsheets 500, 502, 504, 506 containing the updated feedback information can be provided to the data manager device 106, which updates the corresponding column 510 in the source data spreadsheet 508. The spreadsheet 512 containing the modified data 124 can be updated as the updated source data 120 is obtained, or can be updated on a periodic, aperiodic, or on-demand basis.

Returning to the description of the flowchart of the method 400 shown in FIG. 5, at 408, a selection of one or more filters is received. The selected filters can be received by the data manager device 106 based on input received from a user of the data manager device 106. The filters can identify restrictions on which portions of the modified data 124 are to be examined by the data manager device 106. One example of a filter is a date or date range. The user can provide a date or range of dates so that the data manager device 106 only examines the feedback data originated on that date or within that date range. Another example of a filter is a source identifier. The user can identify one or more than one of the sources of the feedback data. The data manager device 106 can then examine the feedback data provided by the identified source(s) while feedback data from other sources is not included in the examination. Another example of a filter is a keyword or more than one keyword. The data manager device 106 can receive one or more than one word from the user, and can search through the contents of the modified data 124. The portions of the modified data 124 that include the keyword(s) identified by the user can be examined by the data manager device 106, while the portions of the modified data 124 that do not include the identified keyword(s) are ignored.

The portions of the feedback data that match or otherwise satisfy the selected filter(s) can be referred to as filtered data. Optionally, the method 400 does not include 408. For example, no filters may be received.

At 410, ontology is applied to the filtered data. Ontology is applied to the feedback information in the filtered data to detect correlation between different expressions of the same or similar theme. Applying the ontology can involve the data manager device 106 searching for and removing special characters from the feedback information in the filtered data. The special characters can be indicia or indicium that are not letters of the alphabet and/or are not numbers. The data manager device 106 can correct spelling in the filtered data by searching for and finding previously identified misspellings of various words or phrases. The data manager device 106 can apply the ontology by reducing the terms appearing in the feedback information of the filtered data. The terms appearing in the feedback information can be reduced by eliminating (or not counting) duplicative entries of the same feedback information (e.g., the exact same feedback provided by the same or different sources, including the same letters, words, misspellings, etc.).

The ontology applied by the data manager device 106 can involve identifying correlations between synonyms appearing in the feedback information of the filtered data. Different words or phrases can be used in the feedback information to express the same idea or concept. For example, the words medicine, medication, pills, script, prescription, Rx, etc., can be used in the same or different feedback information to refer to the same idea or concept (e.g., prescribed medicine). The data manager device 106 can store or access (e.g., from the database 114) a list, table, spreadsheet, or other memory structure, that associates different words or phrases with each other. The associated words can be identified as correlated words or phrases that convey the same or similar meaning. The data manager device 106 can identify correlations between words or phrases in the feedback information of the filtered data by grouping the words or phrases having the same or similar meaning with each other.

The data manager device 106 can apply the ontology to the filtered data by replacing correlated words or phrases with a primary word or phrase. With respect to the preceding example, the data manager device can replace all instances of the words medicine, medication, pills, script, prescription, Rx, etc., in the filtered data with "prescribed medicine." The filtered data can be referred to as correlated data after the ontology is applied by the data manager device 106.

Applying the ontology to the filtered data can resolve many issues that otherwise could prevent of significantly hinder analysis of the unstructured data of the filtered data. Because different persons providing the feedback may use different words or phrases to provide the same meaning, examination of the filtered data (without applying the ontology) may not identify repeated expressions of the same complaint. Additionally, misspellings in the feedback can prevent the data manager device 106 from identifying repeated expressions of the same complaint.

At 412, one or more than one trend in the correlated data is detected. The data manager device 106 can examine the correlated data to determine if the same or similar theme frequently appears in the feedback. This can indicate that a large number of customers or other persons are complaining about the same product, service, etc. Optionally, the data manager device 106 can examine the correlated data to determine if the same or similar theme is appearing more or less often in the feedback. This can indicate that the number of customers or persons complaining about the same product, service, etc., is increasing with respect to time or decreasing with respect to time.

In one embodiment, the data manager device 106 examines the correlated data to identify multiple word phrases and single words that are repeated often. These multiple word phrases and words can be referred to as multiple word phrases of interest or words of interest, respectively.

In one embodiment, a word or phrase of interest can include a contextual placeholder. For example, a phrase of interest can include the contextual placeholder [MEDICAL CONDITION] within one or two words of "refill" (and derivations thereof). This can allow for the type of confidential information appearing in feedback to be analyzed in the same way as confidential information would be analyzed (as described below), without revealing the confidential information to operators or users that do not have a sufficient access level to view the confidential information. This can allow the results of the analysis of the feedback data to be output or otherwise communicated (e.g., via the network 104) to one or more operators or users that cannot view the confidential information. For example, an operator of a website for a pharmacy benefit manager may not be allowed to view confidential medical information of people complaining about a script on the website not working. The presence of confidential medical information in the feedback (as indicated by a contextual placeholder instead of the details of the confidential information) can assist the operator in identifying and resolving the problem with the website. The operator may be able to determine that a script on the website that receives user input for questions about health issues is not working. Without having the contextual placeholder, the feedback information may not provide enough information to allow the operator to determine which script needs repair.

The data manager device 106 can review the correlated data to determine which three word phrases are repeated more often than one or more than one other three word phrases. The data manager device 106 can identify a designated number (e.g., 250, 100, 50, etc.) of the most-often appearing three word phrases in the correlated data as a first set of multiple word phrases of interest in one embodiment.

The data manager device 106 can then examine the correlated data to identify smaller word phrases that are repeated often. For example, the data manager device 106 can review the correlated data to determine which two word phrases are repeated more often than one or more than one other two word phrases. The data manager device 106 can identify a designated number (e.g., 250, 100, 50, etc.) of the most-often appearing two word phrases in the correlated data as a second set of multiple word phrases of interest in one embodiment.

The data manager device 106 can rectify duplication of the multiple word phrases of interest that were identified. For example, many of the three word phrases of interest can include many of the two word phrases of interest. The data manager device 106 can remove the two word phrases from the identified three word phrases.

The data manager device 106 can then examine the correlated data to identify smaller word phrases of interest that are repeated often. For example, the data manager device 106 can review the correlated data to determine which single words of interest appear more often than other words. The data manager device 106 can identify a designated number (e.g., 250, 100, 50, etc.) of the most-often appearing single words in the correlated data as a set of single word phrases in one embodiment.

The data manager device 106 can rectify duplication of the single words of interest that were identified. For example, many of the two word phrases of interest identified by the data manager device 106 can include many of the single words of interest that also were identified by the data manager device 106. The data manager device 106 can remove the single words of interest from the identified two word phrases of interest.

The data manager device 106 can combine the multiple and single word phrases of interest into a corpus of interest. The corpus of interest includes the words and phrases that appear in the filtered feedback data most often, or at least more often than one or more than one other word or phrase. The data manager device 106 examines the words and phrases in the corpus of interest to identify any trends appearing in the words or phrases. For example, the phrase "EXPRESS SCRIPTS website" may be used more and more often over the previous thirty days in the corpus of interest, while the phrase "website not working" may appear less and less often over the previous thirty days in the corpus of interest. These can indicate that the phrase "EXPRESS SCRIPTS website" has an increasing trend, while the phrase "website not working" has a decreasing trend.

At 414, output is generated based on the trends that were detected. The output can be generated by the data manager device 106 creating one or more than one signal that is communicated to an output device, such as a touchscreen, other display device, printer, speaker, or the like. The signal can direct the output device to visually present on the display, audibly present via the speaking, and/or to print information representative of the trends that were detected. The output can serve as a notification to an operator or user of the trends that were identified.

In one embodiment, the output that is generated can include a control signal that directs a device to perform one or more responsive actions. For example, if the data manager device 106 determines that a trend in the feedback indicates that a website, portion of a website (e.g., a script or page within the website), mobile application, call center, or the like, is not working or has other problems, the data manager device 106 can generate and communicate a control signal to a computer server to automatically deactivate or reset the website, mobile application, telephone, or the like. This can result in the problem potentially being automatically fixed or prevented from causing further problems until fixed.

Figure 7:
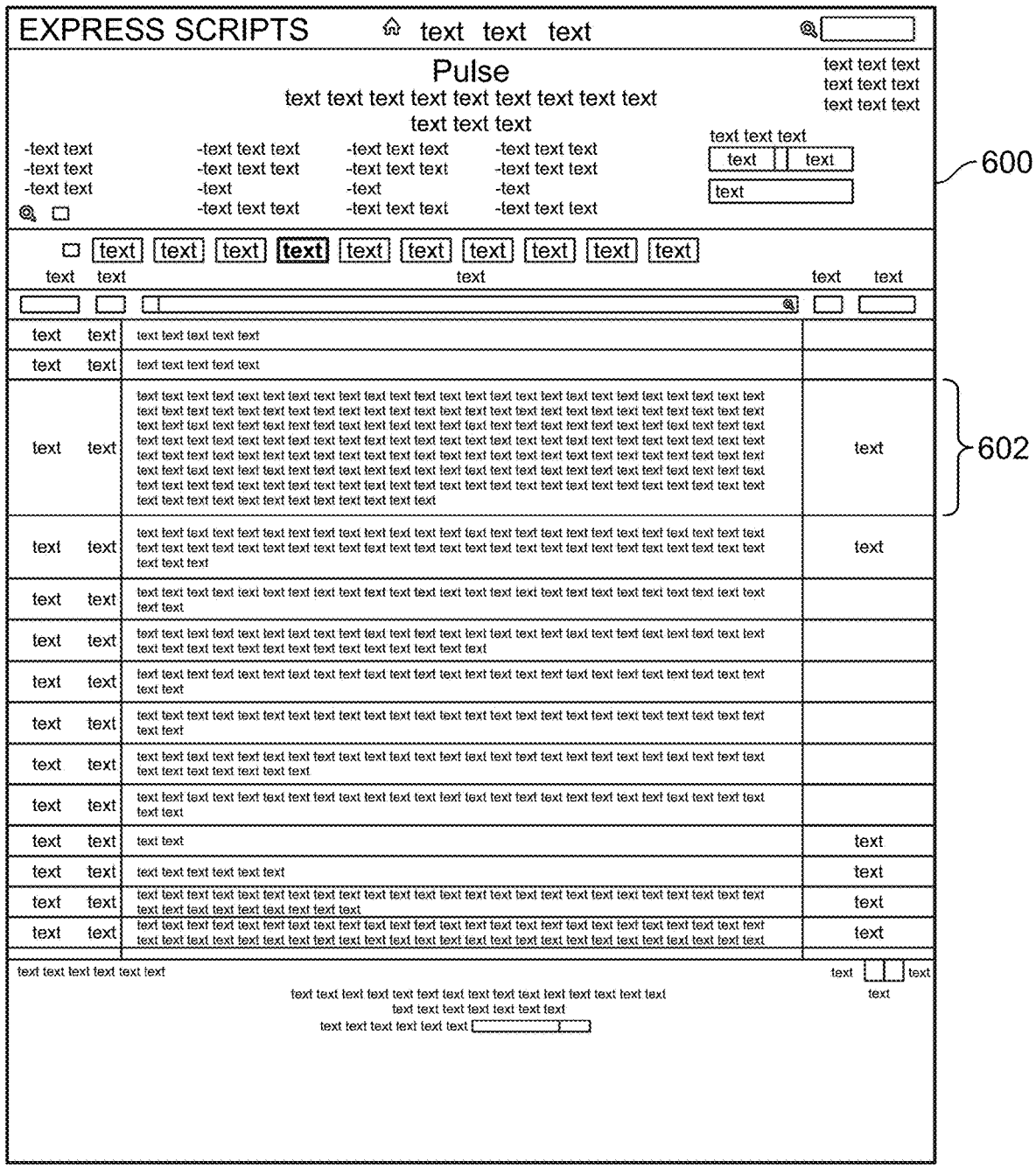
FIG. 7 illustrates one example of a graphical user interface that is generated by a data manager device shown in FIG. 1 to provide an output based on detected trends.

FIG. 7 illustrates one example of a graphical user interface 600 that is generated by the data manager device 106 to provide an output based on the detected trends. The interface 600 can be shown on a display device and/or printed onto a page. The interface 600 visually presents portions 602 of the filtered feedback data identified by the data manager device 106 as including at least some of the multiple word phrases of interest or words of interest. The phrases and/or words of interest can be highlighted or otherwise presented in a different manner for easier recognition of a user of the data manager device 106. Because the filtered feedback data has the confidential information removed (e.g., at 406), the user can read through the feedback data that includes the phrases and/or words of interest without reading confidential information. Optionally, if the user is associated with an access level that grants the user access to the confidential information, the filtered feedback data shown in the interface 600 can include the confidential information (instead of the contextual placeholders). The interface 600 allows for the user to read through the filtered feedback data that is relevant to the inquiry of the user, as expressed by the filters provided by the user.

Figure 8:
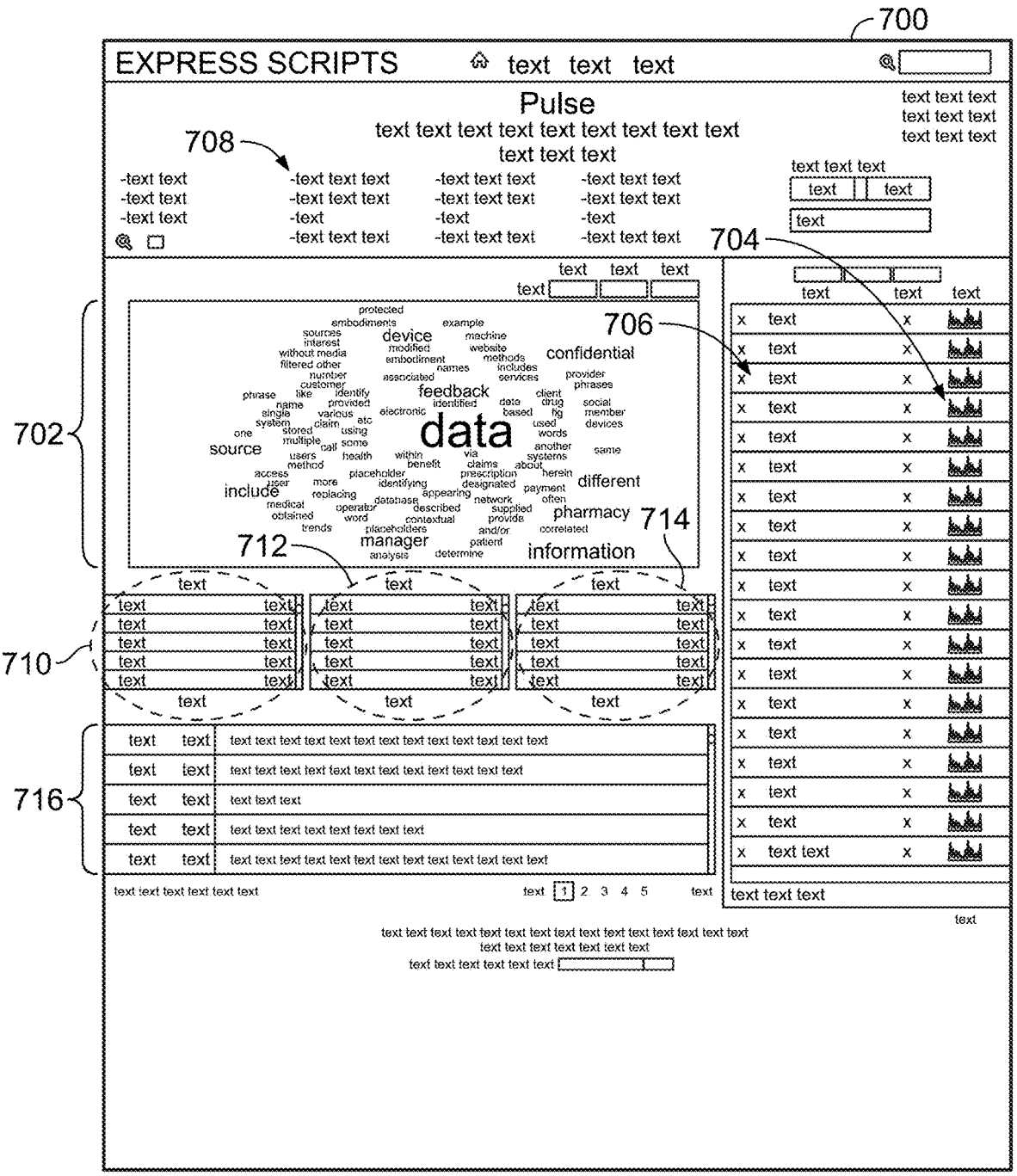
FIG. 8 illustrates another example of a graphical user interface that is generated by the data manager device shown in FIG. 1.

FIG. 8 illustrates another example of a graphical user interface 700 that is generated by the data manager device 106. The interface 700 can be shown on a display device and/or printed onto a page. The interface 700 visually presents a word cloud 702 that reflects relative frequencies of use of the words and phrases of interest. Words or phrases of interest that appear larger in the word cloud 702 occur more often in the correlated data than words or phrases of interest occurring less often in the correlated data. The word cloud 702 provides the user with a quick representation of the words or phrases matching the filters supplied by the user and appearing more often in the feedback data.

The interface 700 also includes several graphs 704 next to separate words or phrases of interest 706. The graphs 704 indicate trends in appearances of the corresponding word or phrase of interest 706. The graphs 704 can allow for a user to see which words or phrases are appearing more often in the feedback over time, and which are appearing less often. For example, each graph 704 can represent how often different words or phrases of interest 706 are used over time. The graphs 704 can be shown alongside horizontal axes representative of time and vertical axes representative of frequencies of usage of the corresponding word or phrase of interest 706. Increases or peaks in a graph 704 indicate that usage of the corresponding word or phrase of interest 706 is increasing in the feedback with respect to time, while decreases or valleys in a graph 704 indicate that appearance of the corresponding word or phrase of interest 706 in the feedback is decreasing with respect to time.

Several selectable boxes or input indicia 708 are associated with different filters. The user can select one or more of the indicia 708 to restrict which portions of the modified data or source data (if the user has a sufficient access level to view the original source data) are being examined. In the illustrated embodiment, each indicium 708 represents a different source of the feedback data, and can be selected to include or de-selected to exclude that feedback data from examination by the data manager device 106. For example, a user can select a single indicium 708, and the graphs 704 and phrases of interest 706 are updated by the data manager device 106 to show only the trends in usage of the phrases of interest 706 obtained or based on data obtained from the source associated with the indicia 708 selected by the user. The user optionally can select multiple indicium 708, and the graphs 704 and phrases of interest 706 are updated by the data manager device 106 to show only the trends in usage of the phrases of interest 706 obtained or based on feedback data obtained from the sources associated with the indicium 708 selected by the user. This can allow the user to determine whether any particular sources of the feedback data exhibit a larger, smaller, or different trend in the phrases of interest 706 than one or more (or all) other sources.

The data manager device 106 can display one or more top phrase lists 710, 712, 714 in the interface 700. Although three top phrase lists 710, 712, 714 are shown in FIG. 8, the interface 700 optionally can include a single list, two lists, or more than three lists. The lists 710, 712, 714 display the phrases of interest that appear most often (relative to other phrases of interest 706) in the relevant list 710, 712, 714 and in the feedback data from the sources selected by the user using the indicium 708. The list 710 displays the most often appearing single-word phrases of interest in the feedback data, the list 712 displays the most often appearing two-word phrases of interest in the feedback data, and the list 714 displays the most often appearing three-word phrases of interest in the feedback data. The lists 710, 712, 714 can be examined by a user to easily and quickly determine which words or phrases are appearing most often in the feedback data from the selected sources. The lists 710, 712, 714 may be updated periodically, upon demand by the user, and/or in real time (e.g., as the feedback data is updated, the lists 710, 712, 714 may be updated).

The data manager device 106 can display excerpts 716 of the modified data in the interface 700. The excerpts 716 include the details of the modified data associated with the sources selected by the user, with one or more phrases of interest 706 selected by the user, with one or more words or phrases in the word cloud 702 selected by the user, or the like. The excerpts 716 display the feedback from the sources, but with the confidential information removed (as described herein). The excerpts 716 may be updated periodically, upon demand by the user, and/or in real time (e.g., as the feedback data is updated, the excerpts 716 may be updated).

Additional graphs or other visualizations of trends in the words or phrases of interest can be generated by the data manager device 106. The data manager device 106 can provide a copy of the correlated data associated with the words or phrases of interest to the user so that the user can perform further review or analysis of the data. Optionally, the data manager device 106 can send e-mails or other electronic communications with summaries of the trends in the words or phrases of interest to users.

Figure 9:
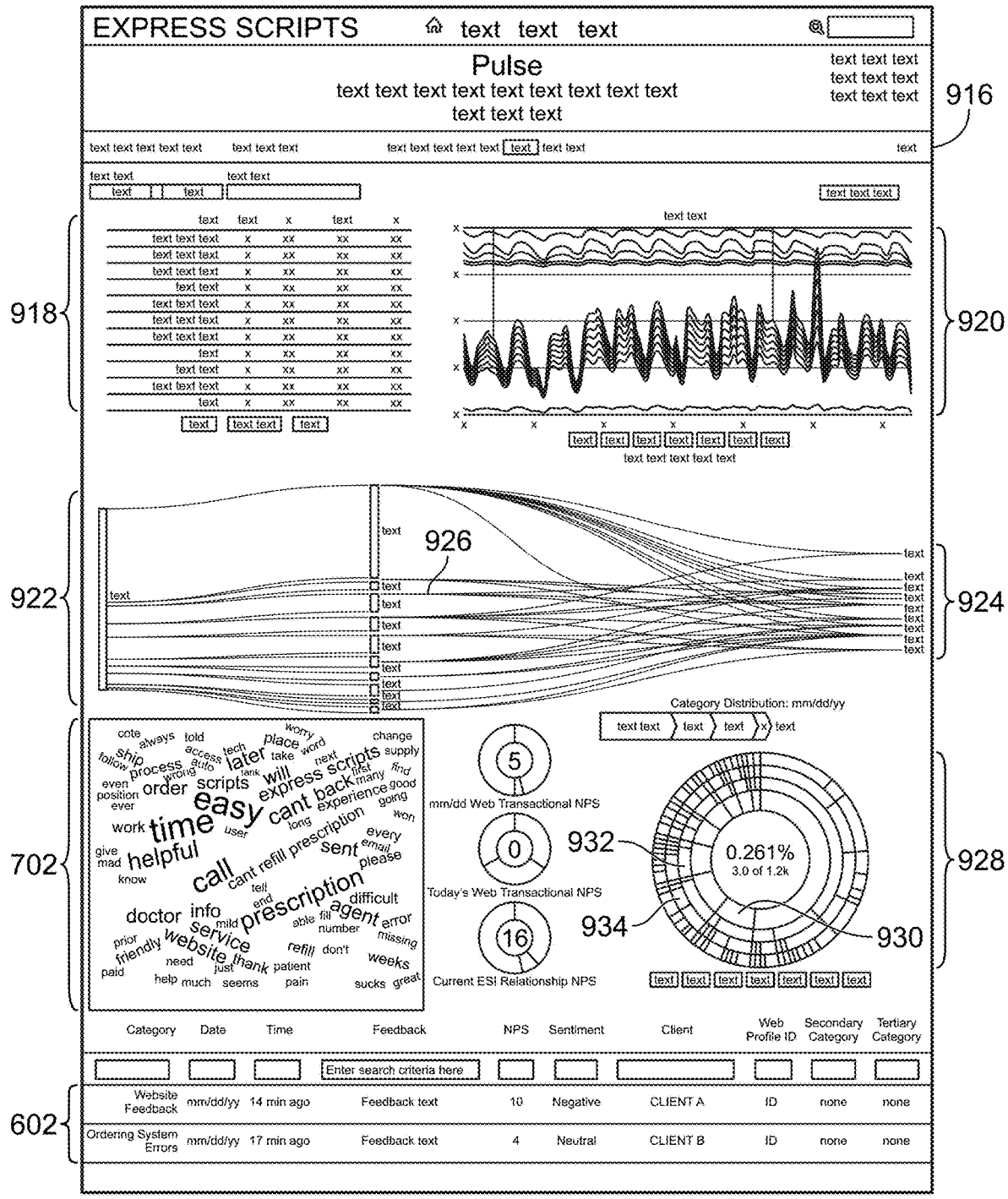
FIG. 9 illustrates another example of a graphical user interface that is generated by the data manager device.

FIG. 9 illustrates another example of a graphical user interface 916 that is generated by the data manager device 106. The interface 916 can be shown on a display device and/or printed onto a page. The interface 916 visually presents information on how often various phrases of interest appear in the source data 120. The interface 916 includes a categorical listing 918 of several categories of phrases of interest. This listing 918 can be a table, list, or other structure that lists several different categories of the phrases of interest. Instead of listing the actual phrases of interest, the data manager device 106 arranges phrases of interest into different groups based on the information associated with the different phrases of interest. This arranging can include counting the number of instances of the phrases of interest, saving copies of the source data 120 having the phrases of interest in different locations, or moving portions of the source data 120 associated with the phrases of interest to different locations based on which phrases of interest appear in the different portions of the source data 120.

For example, the phrases of interest relating to complaints about a mobile app are arranged or organized into a first group by the data manager device 106, the phrases of interest relating to complaints about a website are arranged or organized into a different, second group by the data manager device 106, the phrases of interest relating to complaints about payment are arranged or organized into a different, third group by the data manager device 106, and so on. The listing 918 can provide text identifying these different categories or groups of phrases of interest, and the data manager device 106 can determine various statistical analytics of the phrases of interest. For example, the data manager device 106 can calculate how often the phrases of interest in a category are found in the source data obtained within a designated time period (e.g., today, the previous week, the previous month, and so on). The number of instances of the different categories of phrases of interest can be displayed, along with the percentage change, percentage of total numbers of phrases of interest detected, etc., in the listing 918.

The data manager device 106 also causes an aggregate appearance graph 920 to be shown in the interface 918. The graph 920 shows how many instances of the phrases of interest in the different categories were detected in a user-selected period of time, along with an aggregate (e.g., total) of all instances of the phrases of interest. The data manager device 106 can cause a bar graph 922 to be shown that illustrates how many instances of the phrases of interest associated with the different categories were discovered in the source data 120. The data manager device 106 can illustrate crossover relationships between phrases of interest appearing in different categories. For example, the data manager device 106 can direct the display to present a list 924 of phrases of interest, with the phrases of interest visually coupled with the different categories by lines 926. This can assist a user in determining which categories certain phrases of interest appear in by determining which categories the phrases of interest are connected with by the lines 926. Optionally, another word cloud 702 and/or excerpts 602 of the modified data 124 may be displayed, as shown in FIG. 9.

The data manager device 106 can generate one or more sunburst charts 928 that illustrate hierarchical relationships between various categories of phrases of interest. For example, the chart 928 can have several concentric rings, with each ring representing relative amounts or percentages of the source data 120 related to different categories of phrases of interest. Inner rings can represent larger categories of feedback, such as customer service, website reviews, etc. A user can select part of an inner ring 930 associated with a category (e.g., customer service), and the data manager device 106 can update the next outer ring 932 with relative amounts or percentages of sub-categories of the feedback within the selected category of the inner ring. For example, after selecting customer service in the innermost ring 930, the data manager device 106 can display the neighboring outer ring 932 with relative amounts of feedback that is positive, negative, neutral or the like. The user can select part of the outer ring 932 associated with a sub-category (e.g., positive feedback), and the data manager device 106 can update the next outer ring 934 with relative amounts or percentages of sub-categories of the feedback within the selected sub-category of the ring 932. For example, after selecting customer service in the innermost ring, the data manager device 106 can display the neighboring outer ring with relative amounts of feedback that mentions or is related to a service provider, a website, a mobile app, or the like. The user can continue to select or change a selection of different categories or sub-categories within the rings of the chart 928, and the data manager device 106 can update the outer rings to reflect the relative amounts or percentages of sub-categories of feedback.

Figure 10:
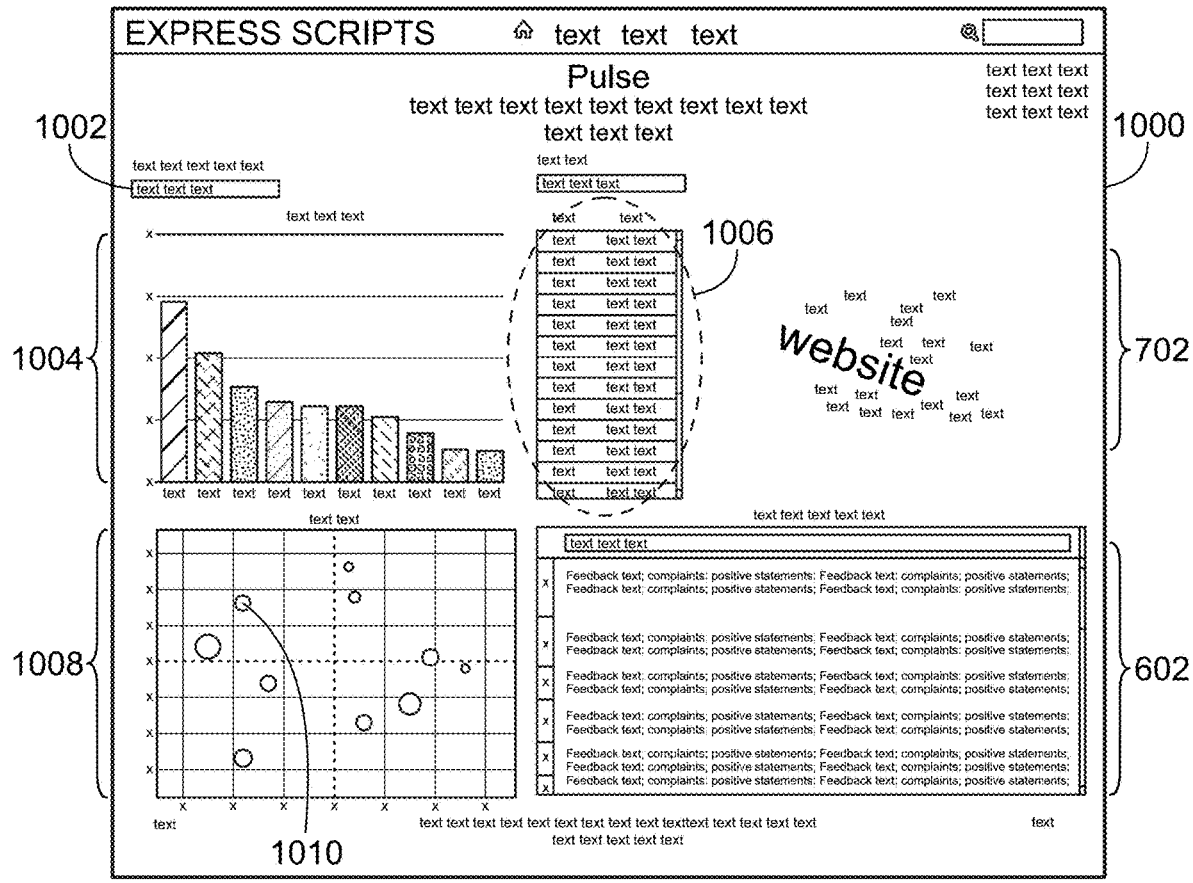
FIG. 10 illustrates another example of a graphical user interface that is generated by the data manager device.
Figure 12:
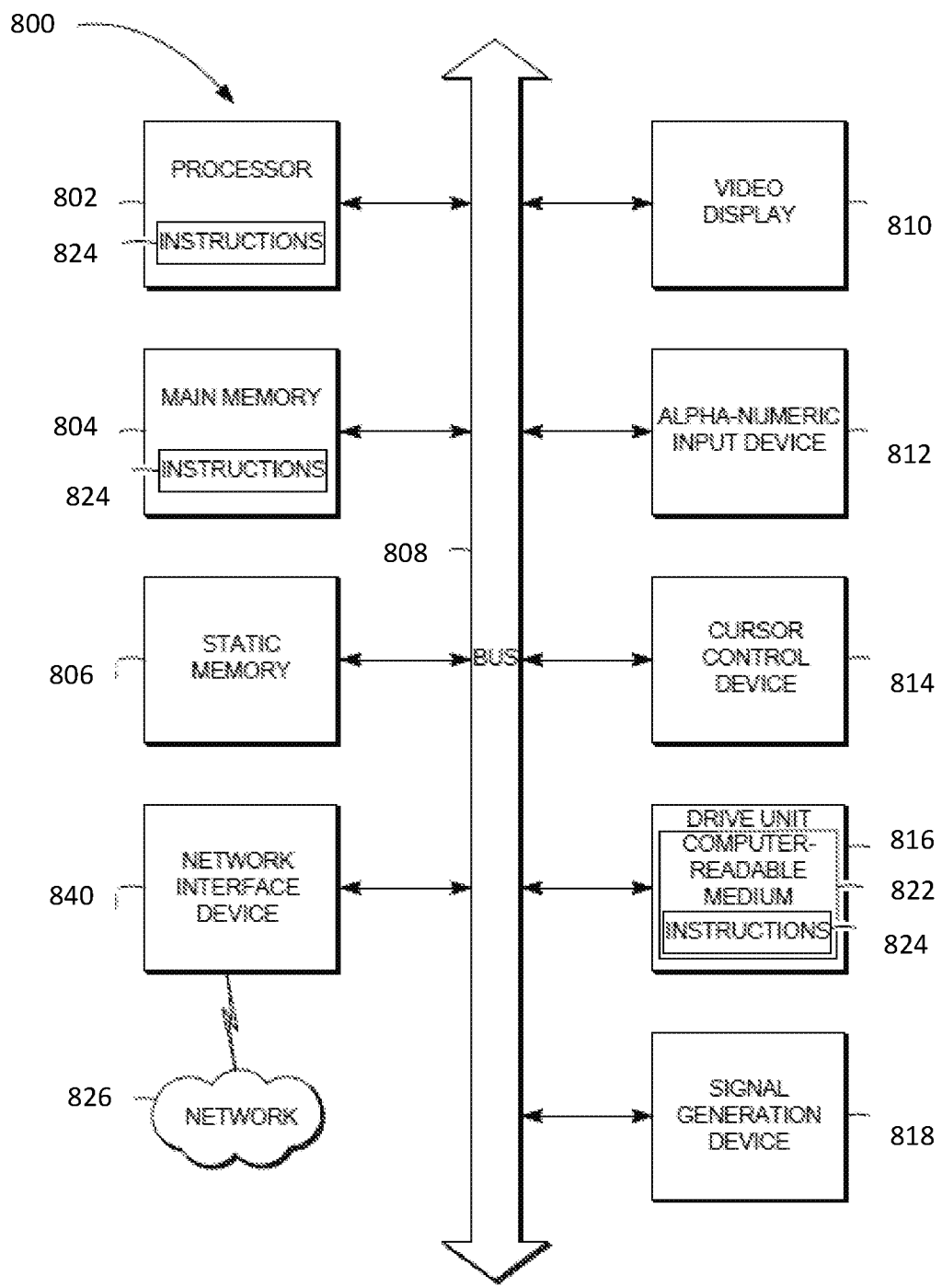
FIG. 12 shows a block diagram of a machine in the example form of a computer system within which a set of instructions may be executed causing the machine to perform anyone or more than one of the methods, processes, operations, or methodologies discussed herein.

FIG. 10 illustrates another example of a graphical user interface 1000 that is generated by the data manager device 106. The interface 1000 can be shown on a display device and/or printed onto a page. The interface 1000 presents analyzed, de-identified data (e.g., modified data 124) that is generated by the data manager device 106 according to another example. The interface 1000 may be presented at a device 102, 106, 110, or at a display 810 (FIG. 12, below). A user can select a source of the modified data 124 to view at a selection icon 1002. The distribution of categories of phrases of interest in the source data 120 or modified data 124 from the source that is selected are displayed using a histogram 1004 or another visual representation. The user can change which source or sources are selected, and the data manager device 106 can update the histogram 1004 accordingly.

A weight list 1006 can be determined and presented by the data manager device 106. This weight list 1006 provides the relative amounts, or weights, of how much various words or phrases of interest appear in the source data 120 from the selected source. The weights can be presented as percentages or fractions of the total source data 120 from the selected source. The data manager device 106 optionally can present one or more word clouds 702 and/or excerpts 602 of the modified data 124 obtained from the source that is selected.

The data manager device 106 can present a topic cluster graph 1008. This graph 1008 visually indicates the relative prevalence of various categories of phrases of interest in the source data 120 from the selected source. Circles or clusters 1010 represent different categories of the phrases of interest. Larger clusters 1010 indicate that there are more source data 120 from the selected source that includes phrases of interest within the associated category, while smaller clusters 1010 indicate that there are fewer source data 120 from the selected source that includes phrases of interest within the associated category.

Figure 11A:
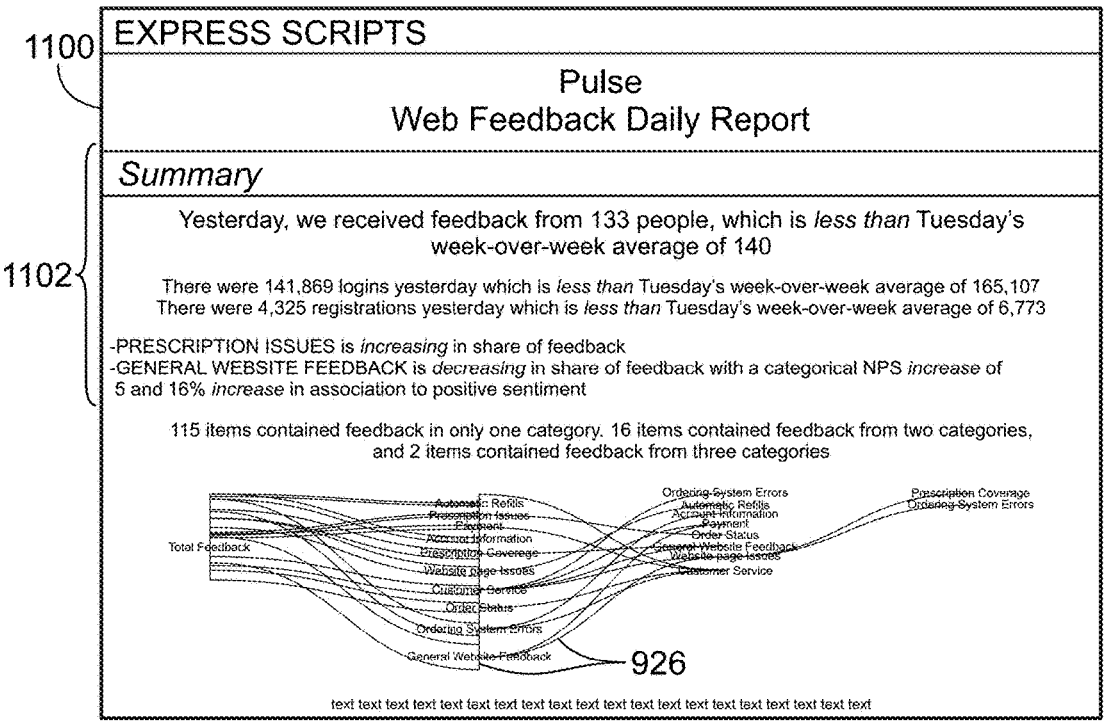
FIGS. 11A-C illustrate another example of a graphical user interface that is generated by the data manager device.
Figure 11C:
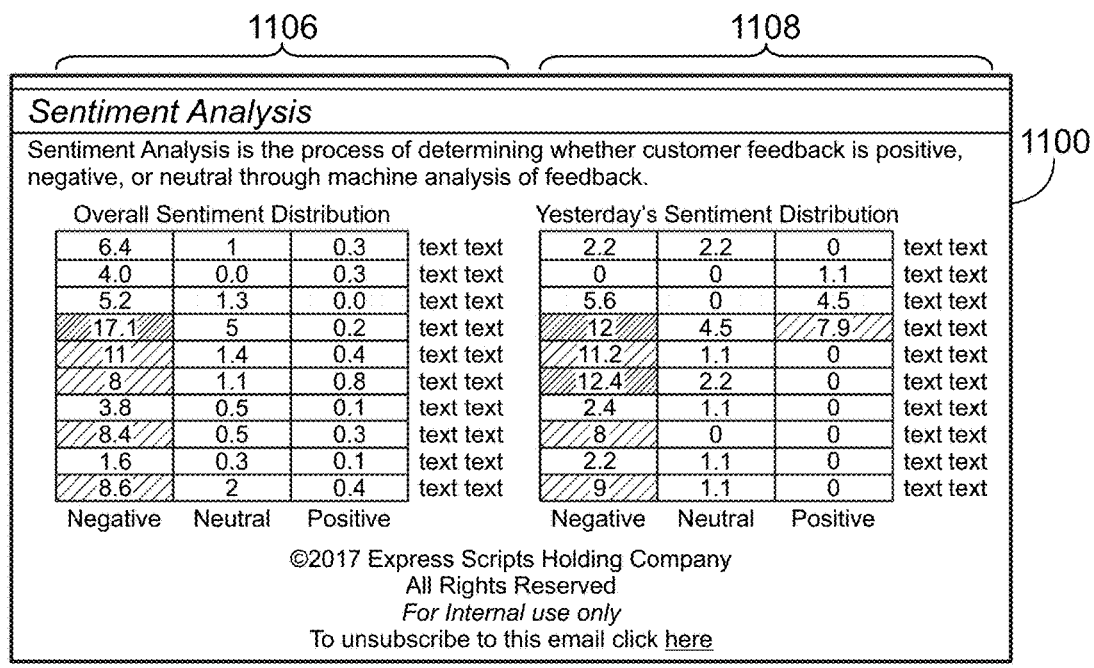
Figure 11B:
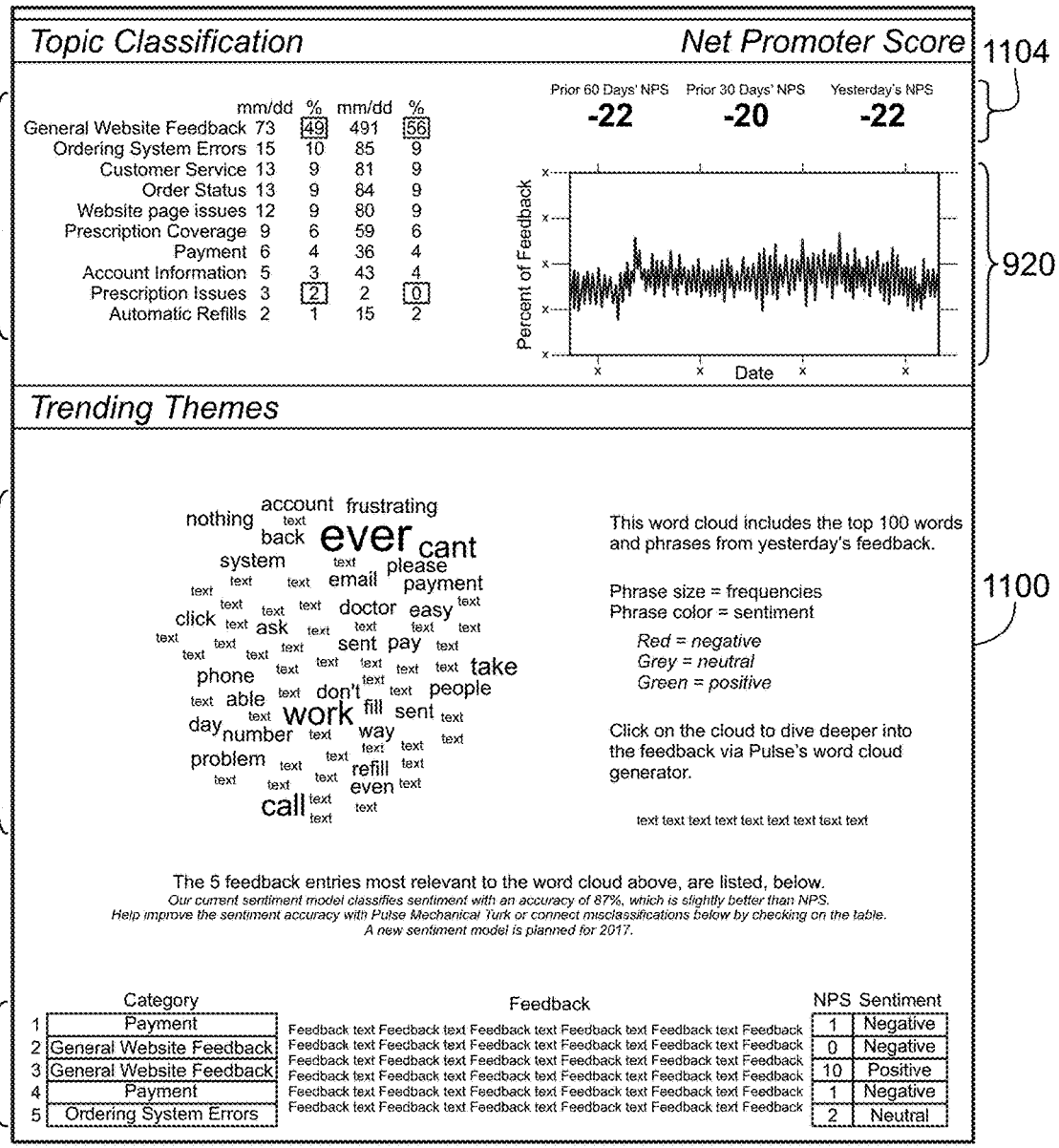

FIGS. 11A-C illustrate another example of a graphical user interface 1100 that is generated by the data manager device 106. FIG. 11A illustrates a top portion of the interface 1100, FIG. 11C illustrates a bottom portion of the interface 1100, and FIG. 11B illustrates a middle portion of the interface 1100 that connects the top and bottom portions of the interface 1100. The interface 1100 can be a daily summary generated by the data manager device 106, and can be automatically shown on a display and/or otherwise communicated to a user device (e.g., via email).

The top portion of the interface 1100 (FIG. 11A) can include a text summary 1102 of changes in the source data 120. For example, the summary 1102 can state the increase or decrease (e.g., a trend) in the feedback received as the source data 120 from one or more sources relative to a previous date or day. The summary 1102 can state the increase or decrease for all source data 120, for the source data 120 from one or more designated sources, and/or may state the increase or decrease in the source data 120 for one or more categories of phrases of interest. The top portion of the interface 1100 optionally can present lines 926 that connect different categories or phrases of interest in the updated source data 120 (e.g., the new source data 120 that has been obtained since the previous summary interface 1100 was provided or generated. The relative thicknesses of the lines 926 can indicate the relative prevalence of the associated phrases of interest in the source data 120.

The middle portion of the interface 1100 (FIG. 11B) can include the categorical listing 918 of several categories of phrases of interest. This listing 918 can be a table, list, or other structure that lists several different categories of the phrases of interest, along with information indication how often the different categories or phrases of interest appear in the source data 120. The listing 918 can indicate the prevalence of the different categories or phrases of interest in the source data 120 during different time periods, such as a recent time period (e.g., the time since the previous summary interface 1100 was generated) and a prior time period (e.g., the week before the current summary interface 1100). This can allow the user to easily determine which categories of interest or phrases of interest are appearing more or less often in the source data 120.

The data manager device 106 can determine and present net promoter scores 1104, which indicate index values ranging from −100 to +100 that indicate how willing customers or users of one or more providers (e.g., one or more sources) are willing to recommend the provider(s) to other customers. The scores 1104 can indicate the score 1104 from the previous day (or other time period), previous month (or other time period), or previous two months (or other time period). The data manager device 106 optionally can present one or more appearance graphs 920, as described above, which can be based on the new source data 120 obtained since the previous summary was generated.

The data manager device 106 can determine and present a word cloud 702 based on the new source data 120 obtained since the previous summary was generated. In one embodiment, the words or phrases appearing in the word cloud 702 can be displayed in different colors, fonts, or the like, based on the connotation associated with the word or phrase. For example, words or phrases appearing in the source data 120 that are associated with negative connotations (e.g., "website not working," "app broken," "wait time too long," etc.) can be presented in the interface 1100 in red font, words or phrases appearing in the source data 120 that are associated with positive connotations (e.g., "website working great," "friendly staff," etc.) can be presented in the interface 1100 in green font, and words or phrases having neither negative nor positive connotations can be presented in the interface 1100 in grey font. Optionally, the data manager device 106 can present excerpts 602 of the source data 120 in the interface 1100.

The bottom portion of the interface 1100 (FIG. 11C) can include sentiment distributions 1106, 1108 of different phrases of interest or categories of the phrases of interest. The distributions 1106, 1108 can be tables, lists, or other structures that provide the different phrases of interest or categories, along with relative amounts or weights of positive connotations, negative connotations, or neutral connotations of the source data 120 associated with the phrases or categories. The distribution 1106 can display the phrases or categories appearing in the source data 120 for a preceding time period (e.g., the previous week, month, year, etc.), while the distribution 1108 can display the phrases or categories appearing in the source data 120 for a shorter time period (e.g., the previous day). These distributions 1106, 1108 can allow a user to quickly and easily see changes in the phrases or categories in the source data 120.

FIG. 12 shows a block diagram of a machine in the example form of a computer system 800 within which a set of instructions may be executed causing the machine to perform anyone or more than one of the methods, processes, operations, or methodologies discussed herein. The one or more than one of the devices 102, 106, 110, 112 may include the functionality of the one or more than one of the computer systems 800.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or a machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform anyone or more of the methodologies discussed herein. Any machine loaded with the instructions is a dedicated machine for executing the present methods.

The example computer system 800 includes a processor or more than one processor 802 (e.g., a central processing unit (CPU) a graphics processing unit (GPU) or both), a main memory 804, and a static memory 806, which communicate with each other via a bus 808. The memories 804, 806 are configured to store machine instructions for executing the methods and processes as described herein. The processor 802 can be discrete components to execute the methods described herein, a programmable logic array loaded with instructions for the methods described herein, an integrated circuited loaded with the instructions for methods described herein. Accordingly, the processor or processors 802 are dedicated to the methods described herein according to an embodiment. The computer system 800 further includes a video display unit 810 (e.g., a liquid crystal display, cathode ray tube, touchscreen, etc.). The computer system 800 also includes an alphanumeric input device 812 (e.g., a keyboard), a cursor control device 814 (e.g., a mouse), a drive unit 816, a signal generation device 818 (e.g., a speaker) and a network interface device 820.

The drive unit 816 includes a computer-readable medium 822 on which is stored one or more sets of instructions (e.g., software 824) embodying anyone or more of the methodologies or functions described herein. The software 824 may also reside, completely or at least partially, within the main memory 804 and/or within the processor 812 during execution thereof by the computer system 800, the main memory 804 and the processor 812 also constituting computer-readable media. The software 824 may further be transmitted or received over a network 826 via the network interface device 820.

While the computer-readable medium 822 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform anyone or more of the methodologies of the present disclosure. The term "computer-readable medium" shall accordingly be taken to include, but not be limited to, solid-state memories, and optical media, and magnetic media. In some embodiments, the computer-readable medium is a non-transitory computer-readable medium.

The present disclosure uses the term patient health information herein to describe protected or regulated medical information. Protected health information may include "individually identifiable health information" held or transmitted by a covered entity or its business associate, in any form or medium, whether electronic, on paper, or oral. Protected health information includes information, including demographic information, which relates to the individual's past, present, or future physical or mental health or condition; the provision of health care to the individual; and the past, present, or future payment for the provision of health care to the individual. Protected health information may also that identify the individual (e.g., a patient) or for which there is a reasonable basis to believe can be used to identify the individual. Protected health information may include many common identifiers (e.g., name, address, birth date, Social Security Number) when such identifiers can be associated with the health information listed above. For example, a medical record, laboratory report, or hospital bill would be protected health information because each document would contain a patient's name and/or other identifying information associated with the health data content.

By contrast, a health plan report that only noted the average age of health plan members was 45 years would not be protected health information because that information, although developed by aggregating information from individual plan member records, does not identify any individual plan members and there is no reasonable basis to believe that it could be used to identify an individual.

The relationship with health information is fundamental to protected health information. Identifying information alone, such as personal names, residential addresses, or phone numbers, would not necessarily be designated as confidential information. For instance, if such information was reported as part of a publicly accessible data source, such as a phone book, then this information would not be protected health information because it is not related to heath data. If such information was listed with health condition, health care provision or payment data, such as an indication that the individual was treated at a certain clinic, then this information would be protected health information. Accordingly, protected health information is individual identifying information and is the type of information that is removed, redacted or replaced with non-identifying indicia using the methods and systems described herein.

The present systems and methods described herein allow for the sharing of data that would normally be subject to protected health information rules with devices and users not qualified to have access to the data by transforming the data into non-protected health data. In an example, all individually identifying information is altered, redacted or removed before the data is shared.

The term "based on" or using, as used herein, reflects an open-ended term that can reflect other elements beyond those explicitly recited.

Certain systems, apparatus, applications or processes are described herein as including several modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. As used herein, "a" or "an" may reflect a single part or multiple parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies. Thus, systems and methods for pharmacy messaging have been described. Although embodiments of the present disclosure have been described with reference to specific example embodiments, it will be evident that various modifications and changes may be made to these embodiments without departing from the broader spirit and scope of the embodiments of the disclosure. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A content analysis system comprising:
   memory hardware configured to store instructions; and
   processor hardware configured to execute the instructions, wherein the instructions include:
   receiving a user request for feedback information from a user device:
   obtaining feedback data associated with the user request from a set of sources;
   aggregating the feedback data to generate source data;
   in response to a user associated with the user device having a first access level acquired from the user request, filtering the source data to generate a set of filtered feedback data according to the first access level;
   in response to the user associated with the user device having a second access level acquired from the user request, filtering the source data to generate the set of filtered feedback data according to the second access level;
   selecting, from the set of filtered feedback data, a subset of filtered feedback data according to a date range specified by the user request;
   applying an ontology to the subset of filtered feedback data to generate transformed feedback data by:
     removing non-alphanumeric characters from the subset of filtered feedback data, removing duplicative terms from the subset of filtered feedback data, identifying designated synonyms appearing in the subset of filtered feedback data, and replacing the designated synonyms with a common word or phrase;

analyzing the transformed feedback data to identify themes;

determining a change in frequency of the identified themes over the specified date range;

generating and transmitting an output to the user device, wherein the output includes a representation that indicates the change in the frequency of the identified themes over the specified date range; and displaying the output via a display of the user device.

2. The content analysis system of claim 1 wherein generating the set of filtered feedback data according to the first access level includes adding feedback data from each source of the set of sources to the set of filtered feedback data.

3. The content analysis system of claim 1 wherein generating the set of filtered feedback data according to the second access level includes:

identifying confidential information in the source data; and performing data substitution replacing the confidential information with contextual placeholders.

4. The content analysis system of claim 3 wherein the confidential information includes patient health information.

5. The content analysis system of claim 3 wherein the performing the data substitution includes at least one of:

determining a name of a person in the source data by comparing the source data with a name database that stores a list of names and replacing the name of the person in the source data with a name placeholder;

determining a location in the source data by comparing the source data with a location database that stores a list of locations and replacing the location in the source data with a location placeholder;

determining a date in the source data by comparing the source data with a date database that stores a list of date formats and replacing the date in the source data with a date placeholder;

determining an electronic address in the source data by comparing the source data with an address database that stores a list of electronic addresses and replacing the electronic address in the source data with an address placeholder; and determining a uniform resource locator address in the source data by comparing the source data with a uniform resource locator database that stores a list of uniform resource locator addresses and replacing the uniform resource locator address in the source data with a uniform resource locator placeholder.

6. The content analysis system of claim 5 wherein the performing the data substitution includes at least one of:

replacing the name of the person in the source data with the name placeholder [NAME];

replacing the location in the source data with the location placeholder [LOCATION];

replacing the date in the source data with the date placeholder [DATE];

replacing the electronic address in the source data with the address placeholder [ELECTRONIC ADDRESS]; and replacing the uniform resource locator address in the source data with the uniform resource locator placeholder [URL].

7. The content analysis system of claim 3 wherein the identifying the confidential information in the source data includes:

parsing the source data; and comparing the parsed source data with a list of designated confidential information.

8. The content analysis system of claim 7 wherein the list of designated confidential information includes at least one of:

a set of words;

a set of phrases;

a set of numbers; and a set of dates.

9. The content analysis system of claim 1 wherein the identifying the theme includes grouping portions of the transformed feedback data together that express a common complaint about a common product or service.

10. The content analysis system of claim 9 wherein the instructions include grouping the portions of the transformed feedback data together that use at least one of: different words, different word phrases, different spellings, and different data formats.

11. A computer-implemented content analysis method comprising:

receiving a user request for feedback information from a user device;

obtaining feedback data associated with the user request from a set of sources;

aggregating the feedback data to generate source data;

in response to a user associated with the user device having a first access level acquired from the user request, filtering the source data to generate a set of filtered feedback data according to the first access level;

in response to the user associated with the user device having a second access level acquired from the user request, filtering the source data to generate the set of filtered feedback data according to the second access level;

selecting, from the set of filtered feedback data, a subset of filtered feedback data according to a date range specified by the user request;

applying an ontology to the subset of filtered feedback data to generate transformed feedback data by:

removing non-alphanumeric characters from the subset of filtered feedback data, removing duplicative terms from the subset of filtered feedback data, identifying designated synonyms appearing in the subset of filtered feedback data, and replacing the designated synonyms with a common word or phrase;

analyzing the transformed feedback data to identify themes;

determining a change in frequency of the identified themes over the specified date range;

generating and transmitting an output to the user device, wherein the output includes a representation that indicates the change in the frequency of the identified themes over the specified date range; and displaying the output via a display of the user device.

12. The content analysis method of claim 11 wherein generating the set of filtered feedback data according to the first access level includes adding feedback data from each source of the set of sources to the set of filtered feedback data.

13. The content analysis method of claim 11 wherein generating the set of filtered feedback data according to the second access level includes:

identifying confidential information in the source data; and performing data substitution replacing the confidential information with contextual placeholders.

14. The content analysis method of claim 13 wherein the confidential information includes patient health information.

15. The content analysis method of claim 13 wherein the performing the data substitution includes at least one of:

determining a name of a person in the source data by comparing the source data with a name database that stores a list of names and replacing the name of the person in the source data with a name placeholder;

determining a location in the source data by comparing the source data with a location database that stores a list of locations and replacing the location in the source data with a location placeholder;

determining a date in the source data by comparing the source data with a date database that stores a list of date formats and replacing the date in the source data with a date placeholder;

determining an electronic address in the source data by comparing the source data with an address database that stores a list of electronic addresses and replacing the electronic address in the source data with an address placeholder; and determining a uniform resource locator address in the source data by comparing the source data with a uniform resource locator database that stores a list of uniform resource locator addresses and replacing the uniform resource locator address in the source data with a uniform resource locator placeholder.

16. The content analysis method of claim 13 wherein the identifying the confidential information in the source data includes:

parsing the source data; and comparing the parsed source data with a list of designated confidential information.

* * * * *